(12) United States Patent
Takagi et al.

(10) Patent No.: US 10,918,325 B2
(45) Date of Patent: Feb. 16, 2021

(54) BRAIN WAVE MEASURING DEVICE AND BRAIN WAVE MEASURING SYSTEM

(71) Applicant: FUJI XEROX CO., LTD., Tokyo (JP)

(72) Inventors: Tomohito Takagi, Kanagawa (JP); Shinji Onishi, Kanagawa (JP); Kengo Tokuchi, Kanagawa (JP); Tsutomu Shiihara, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 488 days.

(21) Appl. No.: 15/659,781

(22) Filed: Jul. 26, 2017

(65) Prior Publication Data

US 2018/0271428 A1    Sep. 27, 2018

(30) Foreign Application Priority Data

Mar. 23, 2017   (JP) .............................. JP2017-057971

(51) Int. Cl.
| | |
|---|---|
| *A61B 5/0484* | (2006.01) |
| *G06F 16/638* | (2019.01) |
| *H04R 1/10* | (2006.01) |
| *A61B 5/00* | (2006.01) |
| *A61B 5/0476* | (2006.01) |
| *G11B 27/031* | (2006.01) |
| *A61B 5/0482* | (2006.01) |
| *A61B 5/0478* | (2006.01) |

(52) U.S. Cl.
CPC .......... *A61B 5/4064* (2013.01); *A61B 5/0004* (2013.01); *A61B 5/0476* (2013.01); *A61B 5/04845* (2013.01); *A61B 5/6803* (2013.01); *A61B 5/6817* (2013.01); *G11B 27/031* (2013.01); *H04R 1/105* (2013.01); *H04R 1/1016* (2013.01); *A61B 5/0478* (2013.01); *A61B 5/0482* (2013.01); *A61B 2560/0214* (2013.01); *A61B 2562/04* (2013.01); *H04R 1/1041* (2013.01); *H04R 2420/07* (2013.01); *H04R 2460/07* (2013.01)

(58) Field of Classification Search
None
See application file for complete search history.

(56) References Cited

U.S. PATENT DOCUMENTS

| | | | | |
|---|---|---|---|---|
| 2007/0112277 A1* | 5/2007 | Fischer | ................ | A61B 5/0006 600/544 |
| 2010/0217100 A1* | 8/2010 | LeBoeuf | .................. | A61B 5/11 600/301 |
| 2012/0197347 A1* | 8/2012 | Olson | ................ | A61N 1/37217 607/60 |

(Continued)

FOREIGN PATENT DOCUMENTS

| | | |
|---|---|---|
| JP | H07-204168 A | 8/1995 |
| JP | 2004-341229 A | 12/2004 |

(Continued)

*Primary Examiner* — Etsub D Berhanu
(74) *Attorney, Agent, or Firm* — Oliff PLC

(57) ABSTRACT

A brain wave measuring device includes a first brain wave measuring unit that contacts an ear of a user, a second brain wave measuring unit, joined to the first brain wave measuring unit, that contacts the ear, and a transmitter that transmits a brain wave measurement result obtained by the first brain wave measuring unit and the second brain wave measuring unit to a terminal device.

19 Claims, 26 Drawing Sheets

(56) References Cited

U.S. PATENT DOCUMENTS

| | | | | |
|---|---|---|---|---|
| 2013/0035578 | A1* | 2/2013 | Chiu | A61M 21/00 600/379 |
| 2013/0343585 | A1* | 12/2013 | Bennett | H04R 25/554 381/315 |
| 2015/0268800 | A1* | 9/2015 | O'Konski | G06F 16/4387 715/716 |
| 2015/0297109 | A1* | 10/2015 | Garten | A61B 5/0482 600/544 |
| 2016/0367204 | A1* | 12/2016 | Won | A61B 5/747 |

FOREIGN PATENT DOCUMENTS

| | | |
|---|---|---|
| JP | 2005-310065 A | 11/2005 |
| JP | 2010-220151 A | 9/2010 |
| JP | 2011-217986 A | 11/2011 |
| JP | 5980931 B2 | 8/2016 |
| WO | 2014/030188 A1 | 2/2014 |
| WO | WO-2016070188 A1 * | 5/2016 ........... A61B 5/0478 |

\* cited by examiner

44

46

US 10,918,325 B2

BRAIN WAVE MEASURING DEVICE AND BRAIN WAVE MEASURING SYSTEM

CROSS-REFERENCE TO RELATED APPLICATIONS

This application is based on and claims priority under 35 USC 119 from Japanese Patent Application No. 2017-057971 filed Mar. 23, 2017.

BACKGROUND

Technical Field

The present invention relates to a brain wave measuring device and a brain wave measuring system.

Summary

According to an aspect of the invention, there is provided a brain wave measuring device including a first brain wave measuring unit that contacts an ear of a user, a second brain wave measuring unit, joined to the first brain wave measuring unit, that contacts the ear, and a transmitter that transmits a brain wave measurement result obtained by the first brain wave measuring unit and the second brain wave measuring unit to a terminal device.

BRIEF DESCRIPTION OF THE DRAWINGS

Exemplary embodiments of the present invention will be described in detail based on the following figures, wherein.

DETAILED DESCRIPTION

Figure 1:
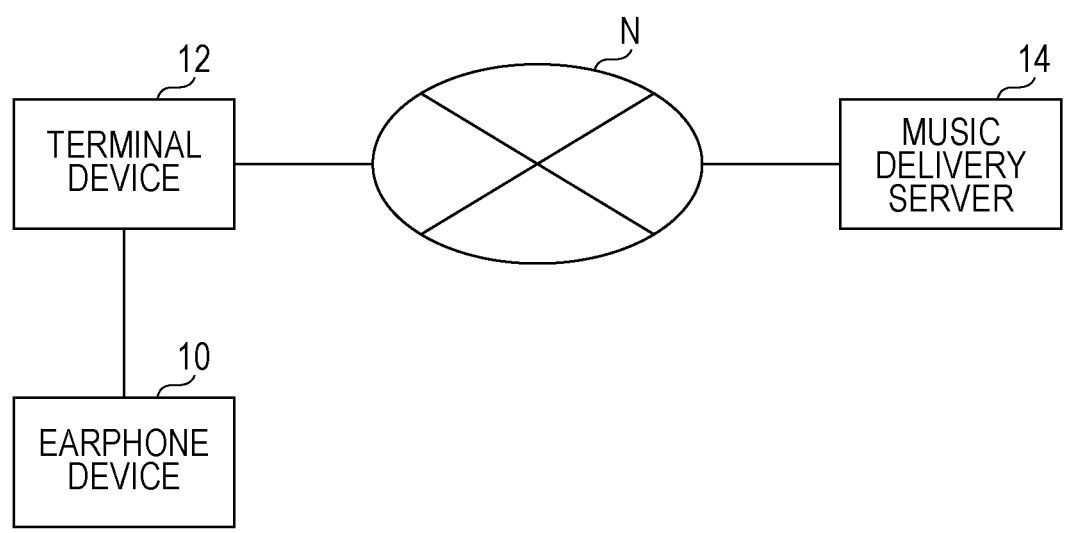
FIG. 1 is a block diagram illustrating an information processing system according to an exemplary embodiment.

An information processing system according to an exemplary embodiment of the present invention will be described with reference to FIG. 1. FIG. 1 illustrates an example of an information processing system according to the present exemplary embodiment.

The information processing system according to the present exemplary embodiment includes, as an example, an earphone device 10, a terminal device 12, and a music delivery server 14.

The earphone device 10 is a pair of canal-type earphones, for example, and is a type of headphones (a device that uses speakers to convert an electrical signal output from a playback device into sound waves) which are used by being inserted into the ears (the external auditory canal). In addition, the earphone device 10 also functions as a brain wave measuring system. Specifically, the earphone device 10 measures the electric potential of the user's head, and outputs information indicating the measurement result (for example, a signal expressing electric potential) as information indicating a brain wave measurement result.

The earphone device 10 is equipped with a wireless communication function. The communication scheme may be, for example, short-range wireless communication (such as Bluetooth (registered trademark) or radio frequency identifier (RFID), for example), infrared communication, visible light communication, Wi-Fi (registered trademark) communication, or the like. The earphone device 10 receives a signal expressing sound (a sound signal such as a speech signal) from the terminal device 12 by wireless communication, and plays back sound in accordance with the signal, for example. Additionally, the earphone device 10 transmits information indicating a brain wave measurement result to the terminal device 12 by wireless communication. Obviously, the earphone device 10 may also be equipped with a wired communication function using a cable. In this case, the earphone device 10 may also receive a sound signal by wired communication to play back sound, and transmit information indicating a brain wave measurement result to an external device by wired communication.

The terminal device 12 is a mobile terminal such as a smartphone, a mobile phone, or a tablet personal computer (PC), or a device such as a PC, a music player, a video playback device, or the like, for example, and corresponds to an example of an information processing device. The terminal device 12 is equipped with a wireless communication function. The terminal device 12 functions as a playback device (a music playback device or a video playback device). For example, the terminal device 12 plays back music, and transmits a sound signal thereof to the earphone device 10 by wireless communication. The terminal device 12 may also play back video, and transmit a sound signal thereof to the earphone device 10 by wireless communication. Additionally, the terminal device 12 receives information indicating a brain wave measurement result from the earphone device 10 by wireless communication, and evaluates the user's brain waves by analyzing the brain wave measurement result. A brain wave measurement result may also be analyzed by the earphone device 10, and information indicating the analysis result may be transmitted from the earphone device 10 to the terminal device 12. A brain wave measurement result may also be analyzed by a device other than the earphone device 10 and the terminal device 12, and information indicating the analysis result may be transmitted to the terminal device 12. The terminal device 12 may also transmit a sound signal to the earphone device 10, and receive information indicating a brain wave measurement result from the earphone device 10, by wired communication using a cable. In addition, the terminal device 12 is equipped with a function of communicating with other devices via a communication link N such as a network. The communication scheme may be wireless communication such as Wi-Fi communication, or wired communication. The terminal device 12 is able to acquire information by connecting to the Internet, for example.

The music delivery server 14 includes a function of communicating with other devices via the communication link N, and is a device that provides a music delivery service via the communication link N. The music delivery server 14 delivers music data over the Internet, for example. The music delivery server 14 may provide music data to users in a downloadable format, or may provide music data to users by streaming delivery. The music data is provided for a fee, for example. The fee may be charged per song or per album, or a subscription fee system may be adopted (for example, a fee system in which a fixed fee is charged per a predetermined period, such as monthly, and during that period, a user is allow unlimited use of the service, or is allowed to use the service with certain limitations). Obviously, music data provided for free may also exist. In addition, various limitations may also be set, such as a limited number of downloads, a limited period for downloading, or a limited period for streaming delivery. The music delivery service may also be usable on a device in which an application (program) for utilizing the music delivery service is installed. The music delivery server 14 may also provide music data for sample listening.

Note that a device that provides a video delivery service (for example, a video delivery server) may also be included in the information processing system. The music delivery server 14 may also double as a video delivery server and provide a video delivery service, or a video delivery server separate from the music delivery server 14 may provide a video delivery service. The video delivery server may provide video data to users in a downloadable format, or may provide video data to users by streaming delivery, for example. The video data is provided for a fee, for example. A fee may be set per video, or a subscription fee system may be adopted. Obviously, video data provided for free may also exist. In addition, various limitations may also be set, such as a limited number of downloads, a limited period for downloading, or a limited period for streaming delivery. The video delivery service may also be usable on a device in which an application (program) for utilizing the video delivery service is installed. The video delivery server may also provide video data for sample viewing.

Obviously, a device that delivers both music and video may also be included in the information processing system.

In the present exemplary embodiment, a user's brain waves are measured by the earphone device 10, and information indicating the measurement result is transmitted to the terminal device 12. In the terminal device 12, the measurement result is analyzed and the user's brain wave state is evaluated. Additionally, a sound signal is transmitted from the terminal device 12 to the earphone device 10, and sound is produced by the earphone device 10. For example, music is played back by the terminal device 12, and sound corresponding to the music is emitted from the earphone device 10. With this arrangement, the user's brain waves while listening to music are measured by the earphone device 10, and the brain wave state is analyzed by the terminal device 12. The playback of music may also be controlled in accordance with the brain wave measurement result. For example, the music to be played back may be changed in accordance with the brain wave state. The music data may be data provided to the terminal device 12 by the music delivery server 14, or data stored in the terminal device 12 without being delivered from the music delivery server 14.

Note that the earphone device 10 may be connected to a different music playback device or video playback device and used without being used together with the terminal device 12, or may be used as a standalone brain wave measuring device without producing sound (in other words, the earphone device 10 may be used as a brain wave measuring device without playing back music or video). In addition, the terminal device 12 may be used as a standalone brain wave analyzing device without being used together with the earphone device 10, and earphones other than the earphone device 10 may be connected. The terminal device 12 may also control the playback of music and video on the basis of brain waves measured by a brain wave measuring device other than the earphone device 10.

Figure 2:
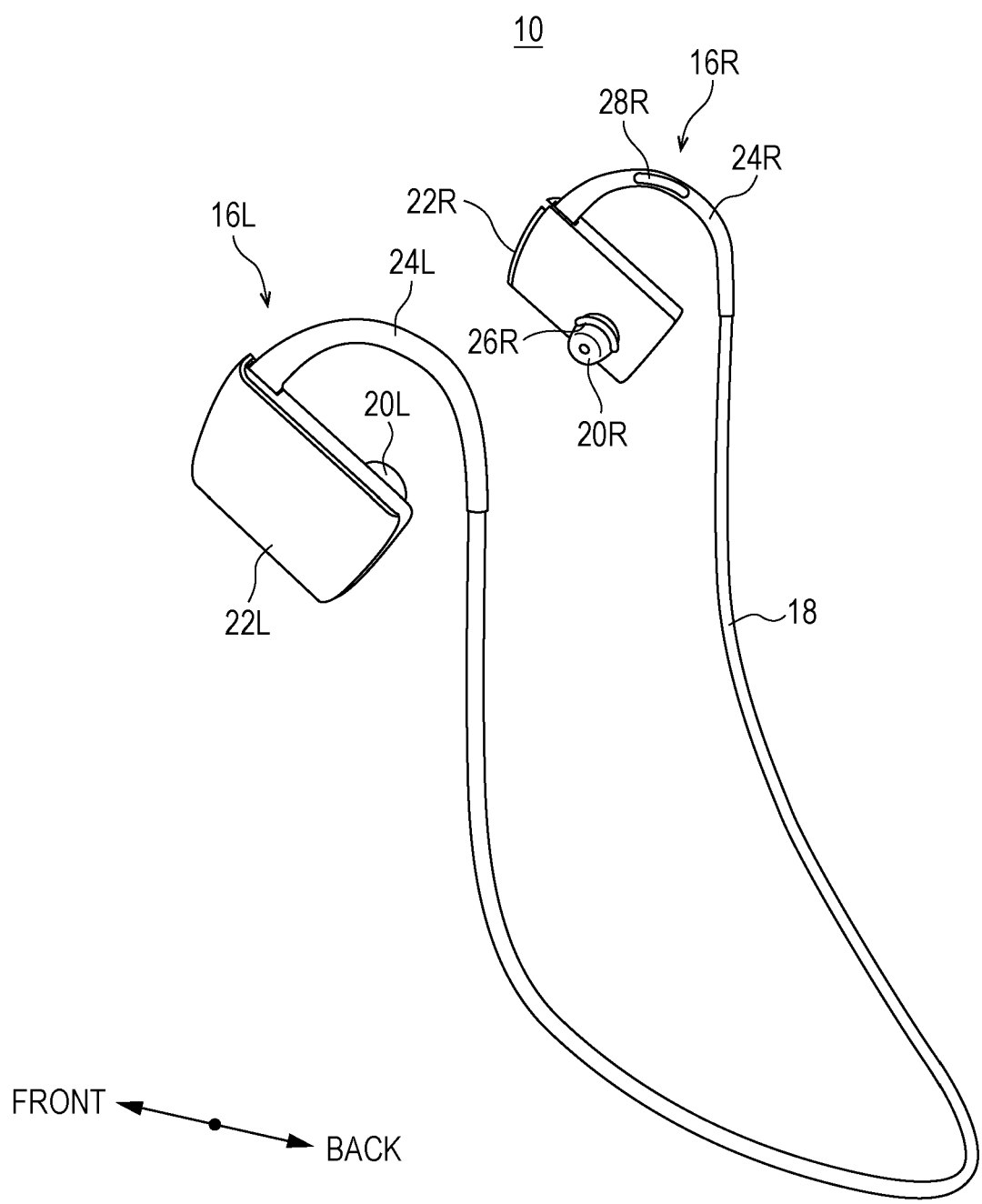
FIG. 2 is a perspective view illustrating an overall configuration of an earphone device.
Figure 3:
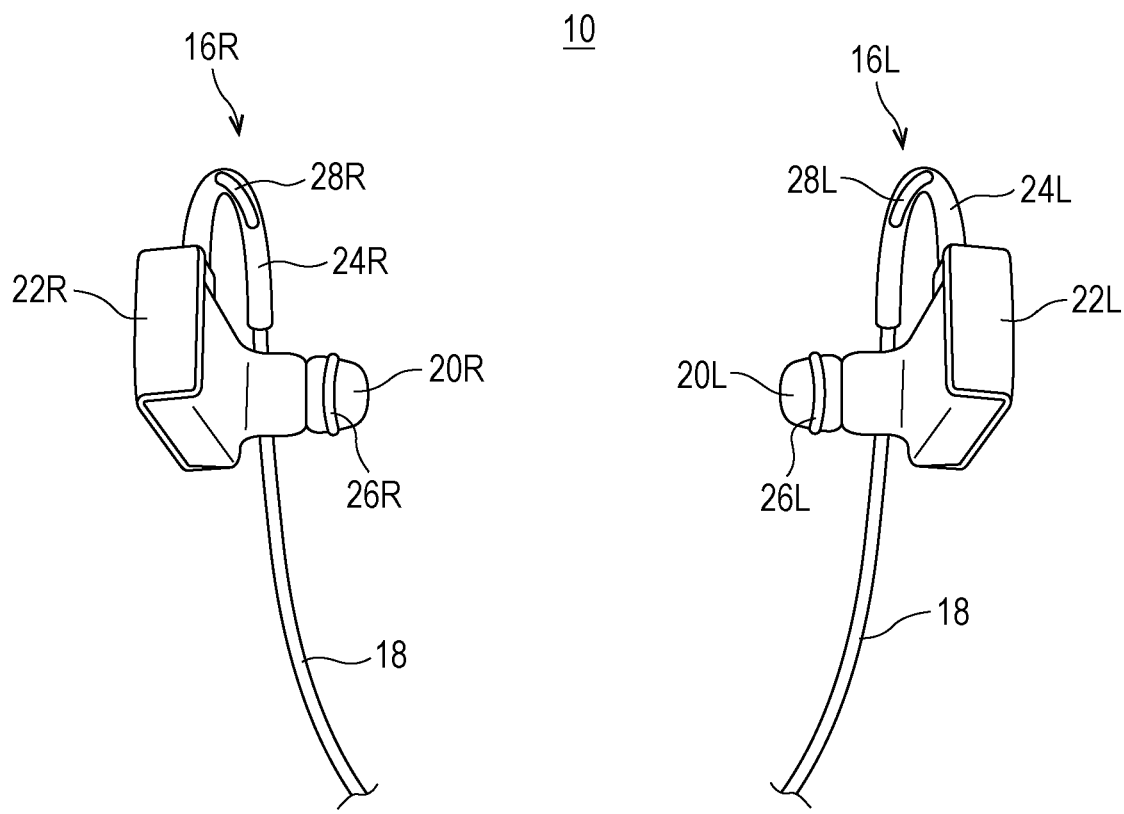
FIG. 3 is a perspective view illustrating a configuration of part of an earphone device.
Figure 4:
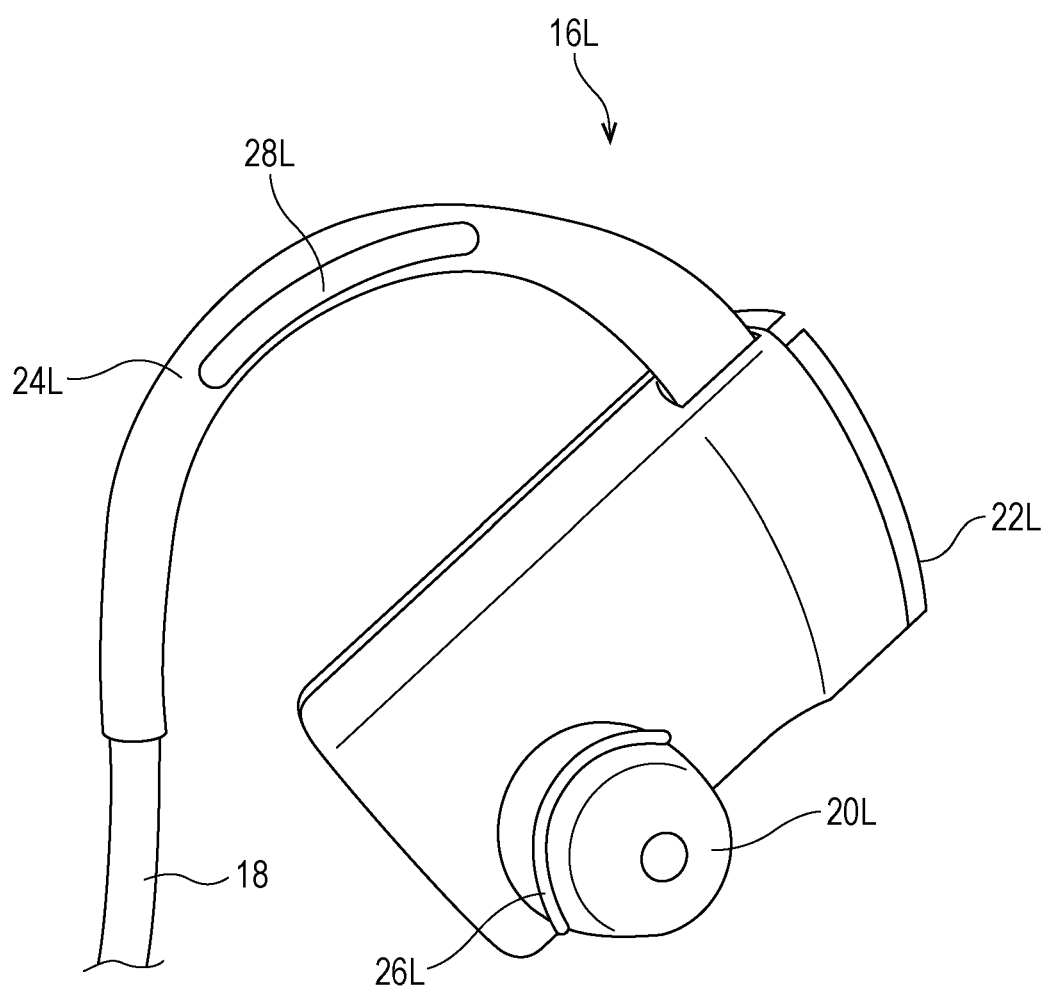
FIG. 4 is a perspective view illustrating a left-side earphone unit.

Hereinafter, the earphone device 10 will be described in detail with reference to FIGS. 2 to 4. FIG. 2 is a perspective view illustrating an overall configuration of the earphone device 10. FIG. 3 is a perspective view illustrating a configuration of part of the earphone device 10, and is a diagram of the earphone device 10 viewed from a different direction than FIG. 2. FIG. 4 is a perspective view illustrating a left-side earphone unit.

Herein, for the sake of convenience, front and back are defined as illustrated in FIG. 2. Front is the direction in which the user's face is pointed, while back is the reverse direction of front.

As illustrated in FIGS. 2 and 3, the earphone device 10 is largely divided into a left-side earphone unit 16L worn on the user's left ear, a right-side earphone unit 16R worn on the user's right ear, and a cable 18 that connects the left-side earphone unit 16L and the right-side earphone unit 16R. Note that the left-side earphone unit 16L corresponds to an example of a first brain wave measuring device, while the right-side earphone unit 16R corresponds to an example of a second brain wave measuring device.

The left-side earphone unit 16L includes a left-side speaker unit 20L which is inserted into the user's left ear (external auditory canal), a left-side support unit 22L (left-side base unit) that supports the left-side speaker unit 20L, and a left-side ear hook unit 24L, one end of which is joined to the left-side support unit 22L.

The left-side speaker unit 20L is made up of components such as a driver unit that produces sound, a sound conduit, an equalizer, a housing (such as a frame or case), and an earpad (earpiece) that covers the part inserted into the ear. Note that the speaker unit of publicly available canal-type earphones can be used as the left-side speaker unit 20L. The earpad of the left-side speaker unit 20L is made of a resin such as rubber, for example.

On the side face of the left-side speaker unit 20L, a first left brain wave sensor 26L is provided. Described in further detail, the first left brain wave sensor 26L is provided on the side face of the earpad constituting the left-side speaker unit 20L. The first left brain wave sensor 26L is an electrode that senses the electric potential of the head together with a second left brain wave sensor 28L described later. The first left brain wave sensor 26L is made up of conductive rubber made from carbon, for example. Note that the first left brain wave sensor 26L corresponds to an example of a first brain wave measuring unit.

The left-side support unit 22L has a thin rectangular cuboid shape as an example, and the left-side speaker unit 20L is installed on the face of the left-side support unit 22L that opposes the user's left ear when the user wears the earphone device 10. The left-side support unit 22L is a case, for example, and houses components such as an electronic circuit board inside.

The left-side ear hook unit 24L has a curved shape overall, and is a member that hooks over the user's left ear when the user wears the earphone device 10. One end of the left-side ear hook unit 24L is connected to the front-side part of the left-side support unit 22L, with the left-side ear hook unit 24L having a shape that curves from the connecting part towards the back side of the left-side support unit 22L, thereby forming a curved part. The curved part hooks over the top of left ear. The other end of the left-side ear hook unit 24L is joined to one end of the cable 18.

The left-side ear hook unit 24L is provided with a second left brain wave sensor 28L along the left-side ear hook unit 24L. The second left brain wave sensor 28L is provided on the face of the left-side ear hook unit 24L that opposes the user's left ear so as to contact the left ear, more specifically the underside of the left ear (a position close to the skull), when the left-side ear hook unit 24L is hooked over the left ear, for example. By providing the second left brain wave sensor 28L so as to contact the underside of the left ear, electric potential is sensed at a position closer to the brain, and the accuracy of brain wave measurement can be raised. The second left brain wave sensor 28L is an electrode that senses the electric potential of the head together with the first left brain wave sensor 26L described above. The second left brain wave sensor 28L is made up of conductive rubber made from carbon, for example. For example, the electric potential sensed by the second left brain wave sensor 28L is used as a reference potential, and the first left brain wave sensor 26L measures the electric potential from the reference potential (potential difference). Note that the second left brain wave sensor 28L corresponds to an example of a second brain wave measuring unit.

When the left-side ear hook unit 24L is hooked over the left ear and the left-side speaker unit 20L is inserted into the left ear, the left ear becomes pinched by the first left brain wave sensor 26L provided on the left-side speaker unit 20L and the second left brain wave sensor 28L provided on the left-side ear hook unit 24L, and in this state, brain waves are measured by the first left brain wave sensor 26L and the second left brain wave sensor 28L.

As above, by pinching the left ear between the first left brain wave sensor 26L and the second left brain wave sensor 28L, the brain wave sensors can be brought into close contact with the left ear, and as a result, the brain wave measuring accuracy can be improved. Also, the first left brain wave sensor 26L is inserted into the left ear, thereby raising the adhesion between the first left brain wave sensor 26L and the left ear.

The right-side earphone unit 16R includes a right-side speaker unit 20R which is inserted into the user's right ear (external auditory canal), a right-side support unit 22R (right-side base unit) that supports the right-side speaker unit 20R, and a right-side ear hook unit 24R, one end of which is joined to the right-side support unit 22R.

Similarly to the left-side speaker unit 20L, the right-side speaker unit 20R is made up of components such as a driver unit, a sound conduit, an equalizer, a housing, and an earpad. Note that the speaker unit of publicly available canal-type earphones can be used as the right-side speaker unit 20R. The earpad of the right-side speaker unit 20R is made of a resin such as rubber, for example.

On the side of the right-side speaker unit 20R, a first right brain wave sensor 26R is provided. Described in further detail, the first right brain wave sensor 26R is provided on the side face of the earpad constituting the right-side speaker unit 20R. The first right brain wave sensor 26R is an electrode that senses the electric potential of the head together with a second right brain wave sensor 28R described later. The first right brain wave sensor 26R is made up of conductive rubber made from carbon, for example. Note that the first right brain wave sensor 26R corresponds to an example of a third brain wave measuring unit.

The right-side support unit 22R has a thin rectangular cuboid shape as an example, and the right-side speaker unit 20R is installed on the face of the right-side support unit 22R that opposes the user's right ear when the user wears the earphone device 10. The right-side support unit 22R is a case, for example, and houses components such as an electronic circuit board inside.

The right-side ear hook unit 24R has a curved shape overall, and is a member that hooks over the user's right ear when the user wears the earphone device 10. One end of the right-side ear hook unit 24R is connected to the front-side part of the right-side support unit 22R, with the right-side ear hook unit 24R having a shape that curves from the connecting part towards the back side of the right-side support unit 22R, thereby forming a curved part. The curved part hooks over the top of right ear. The other end of the right-side ear hook unit 24R is joined to the other end of the cable 18.

The right-side ear hook unit 24R is provided with a second right brain wave sensor 28R along the right-side ear hook unit 24R. The second right brain wave sensor 28R is provided on the face of the right-side ear hook unit 24R that opposes the user's right ear so as to contact the right ear, more specifically the underside of the right ear (a position close to the skull), when the right-side ear hook unit 24R is hooked over the right ear, for example. By providing the second right brain wave sensor 28R so as to contact the underside of the right ear, electric potential is sensed at a position closer to the brain, and the accuracy of brain wave measurement can be raised. The second right brain wave sensor 28R is an electrode that senses the electric potential of the head together with the first right brain wave sensor 26R described above. The second right brain wave sensor 28R is made up of conductive rubber made from carbon, for example. For example, the electric potential sensed by the second right brain wave sensor 28R is used as a reference potential, and the first right brain wave sensor 26R measures the electric potential from the reference potential (potential difference). Note that the second right brain wave sensor 28R corresponds to an example of a fourth brain wave measuring unit.

When the right-side ear hook unit 24R is hooked over the right ear and the right-side speaker unit 20R is inserted into the right ear, the right ear becomes pinched by the first right brain wave sensor 26R provided on the right-side speaker unit 20R and the second right brain wave sensor 28R provided on the right-side ear hook unit 24R, and in this state, brain waves are measured by the first right brain wave sensor 26R and the second right brain wave sensor 28R.

As above, by pinching the right ear between the first right brain wave sensor 26R and the second right brain wave sensor 28R, the brain wave sensors can be brought into close contact with the right ear, and as a result, the brain wave measuring accuracy can be improved. Also, the first right brain wave sensor 26R is inserted into the right ear, thereby raising the adhesion between the first right brain wave sensor 26R and the right ear.

The earphone device 10 is provided with a wireless communication function (for example, Bluetooth), and communicates with the terminal device 12 wirelessly. A communication interface (communication chip) that includes the wireless communication function is built into the left and right earphone units, for example. For example, a communication chip for wireless communication (for example, a communication chip for Bluetooth) is built into the left-side support unit 22L (case) of the left-side earphone unit 16L, while similarly, a communication chip for wireless communication is built into the right-side support unit 22R (case) of the right-side earphone unit 16R. The left-side earphone unit 16L receives a sound signal (left-ear sound signal) transmitted from the terminal device 12 with the communication chip built into the left-side support unit 22L, and produces sound in accordance with the sound signal. The right-side earphone unit 16R receives a sound signal (right-ear sound signal) transmitted from the terminal device 12 with the communication chip built into the right-side support unit 22R, and produces sound in accordance with the sound signal.

In addition, information indicating a brain wave measurement result obtained by the left-side earphone unit 16L and the right-side earphone unit 16R is transmitted from the earphone device 10 to the terminal device 12 by wireless communication (for example, Bluetooth).

The left-side earphone unit 16L and the right-side earphone unit 16R are physically connected by the cable 18, and transmit and receive data with each other through the cable 18.

Both information indicating a brain wave measurement result obtained by the left-side earphone unit 16L and information indicating a brain wave measurement result obtained by the right-side earphone unit 16R may be transmitted respectively from the earphone device 10 to the terminal device 12, or the respective information may be combined by processing such as statistical processing, for example, and then transmitted to the terminal device 12. For the statistical processing, computations such as the simple average or a weighted average of a brain wave measurement result obtained by the left-side earphone unit 16L and a brain wave measurement result obtained by the right-side earphone unit 16R may be conducted in the earphone device 10, for example, and information indicating the processing result may be transmitted from the earphone device 10 to the terminal device 12 by the communication chip installed in either the left-side earphone unit 16L or the right-side earphone unit 16R. Obviously, information before such processing is performed may also be transmitted from the earphone device 10 to the terminal device 12, and such processing may be conducted by the terminal device 12.

For example, in a case in which a fault occurs in the cable 18, and the transmitting and receiving of data between the left-side earphone unit 16L and the right-side earphone unit 16R becomes unavailable, information indicating the brain wave measurement result obtained by each earphone unit may be transmitted respectively to the terminal device 12. In this case, information indicating the brain wave measurement result obtained by the left-side earphone unit 16L is transmitted from the left-side earphone unit 16L to the terminal device 12 by the communication chip installed in the left-side earphone unit 16L. Similarly, information indicating the brain wave measurement result obtained by the right-side earphone unit 16R is transmitted from the right-side earphone unit 16R to the terminal device 12 by the communication chip installed in the right-side earphone unit 16R. By transmitting brain wave measurement results in this way, even if the cable 18 fails, brain wave measurement can continue, and brain wave measurement results can be transmitted to the terminal device 12.

Also, in a case in which the communication chip installed in one of the earphone units fails, the non-faulty communication chip may be used to transmit information indicating a brain wave measurement result to the terminal device 12. In this case, information indicating a brain wave measurement result obtained by the left-side earphone unit 16L and information indicating a brain wave measurement result obtained by the right-side earphone unit 16R may be transmitted respectively to the terminal device 12, or information generated by applying processing such as statistical processing to both sets of information may be transmitted to the terminal device 12. By transmitting brain wave measurement results in this way, even if one of the communication chips fails, brain wave measurement can continue, and brain wave measurement results can be transmitted to the terminal device 12.

In addition, if one of the earphone units fails, information indicating a brain wave measurement result obtained by the other, non-faulty earphone unit may be transmitted to the terminal device 12. By transmitting brain wave measurement results in this way, even if one of the earphone units fails, brain wave measurement can continue, and brain wave measurement results can be transmitted to the terminal device 12.

Note that a failure of the cable 18 or a communication chip is sensed by a sensor, a continuity check, or the like.

A battery that supplies electric power for driving the earphone device 10 is installed in either the left-side earphone unit 16L or the right-side earphone unit 16R. For example, a battery is built into the left-side support unit 22L (case) of the left-side earphone unit 16L, while a battery is not built into the right-side earphone unit 16R. In this case, each unit of the left-side earphone unit 16L (such as the driver unit inside the left-side speaker unit 20L, the communication chip, and components related to brain wave measurement, for example) is driven by received a supply of electric power from the battery. Meanwhile, electric power is supplied from the battery built into the left-side support unit 22L to the right-side earphone unit 16R through the cable 18, and each unit of the right-side earphone unit 16R (such as the driver unit inside the right-side speaker unit 20R, the communication chip, and components related to brain wave measurement, for example) are driven by the electric power. A battery may also not be provided in the left-side earphone unit 16L, and instead may be provided in the right-side earphone unit 16R. In this case, electric power likewise is supplied from the right-side earphone unit 16R to the left-side earphone unit 16L through the cable 18. Charging of the battery may be conducted via a USB cable, or by wireless charging when the earphone device 10 is housed in a case, for example. Note that batteries may also be provided in both the left-side earphone unit 16L and the right-side earphone unit 16R.

Note that to keep battery charging from influencing the electric potential measurement, the electric potential measurement may be stopped when charging is started. As another example, in a case in which a shield member (anti-electromagnetic wave member) is provided around the battery and charging-related components, the electric potential measurement may be conducted even during charging.

The earphone device 10 may also be provided with an operating unit such as a remote control.

Figure 5:
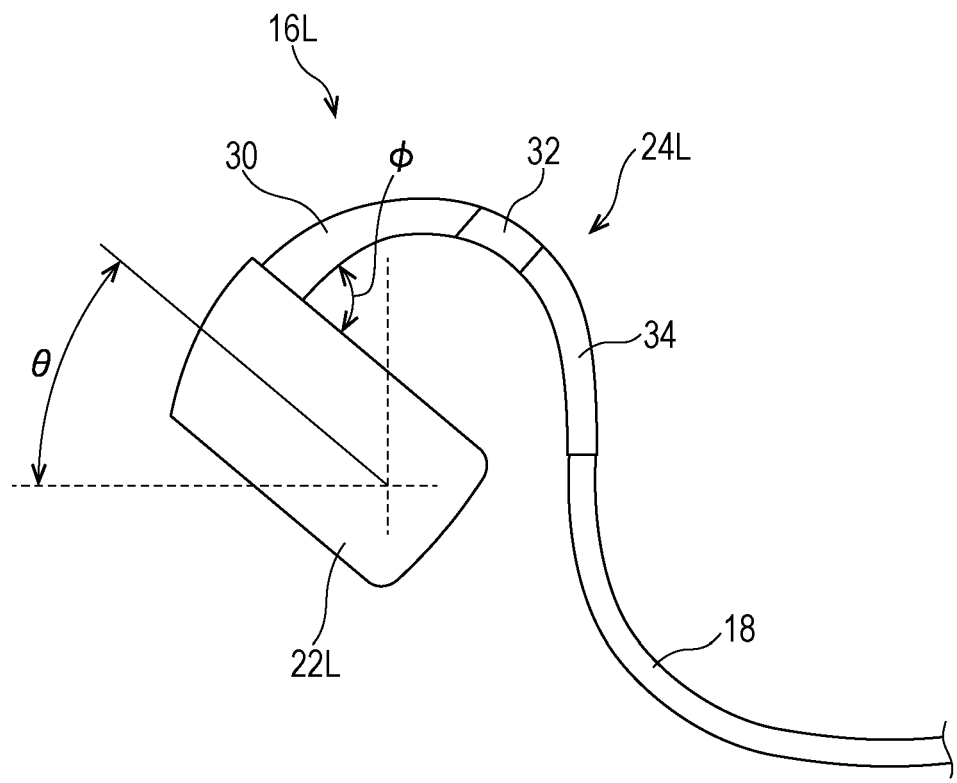
FIG. 5 is a perspective view illustrating a right-side earphone unit.

Hereinafter, features such as the shape of the ear hook units will be described in further detail, with reference to FIG. 5. FIG. 5 is a diagram of the left-side earphone unit 16L as viewed from the left-side support unit 22L side.

The left-side ear hook unit 24L includes a first curved part 30 having a first curvature, a second curved part 32 having a second curvature, and a third curved part 34 having a third curvature. One end of the first curved part 30 is connected to the left-side support unit 22L. The first curved part 30 is a member provided from the left-side support unit 22L to the second curved part 32. One end of the second curved part 32 is connected to the other end of the first curved part 30. The second curved part 32 is a member provided from the connecting portion to the third curved part 34. One end of the third curved part 34 is connected to the other end of the second curved part 32. The third curved part 34 is a member provided from the connecting portion to the cable 18. The other end of the third curved part 34 is connected to the cable 18. Note that the first curved part 30, the second curved part 32, and the third curved part 34 are integrated, thereby forming the left-side ear hook unit 24L. Obviously, the first curved part 30, the second curved part 32, and the third curved part 34 may also be configured by respectively different members and connected to each other.

The first curvature of the first curved part 30 is from R12.5 to R14.5, for example. The first curvature of the first curved part 30 may also be from R13.0 to R14.0, and may be R13.5. The second curvature of the second curved part 32 is from R15.5 to R17.5, for example. The second curvature of the second curved part 32 may also be from R16.0 to R17.0, and may be R16.5. The third curvature of the third curved part 34 is from R106.5 to R108.5, for example. The third curvature of the third curved part 34 may also be from R107.0 to R108.0, and may be R107.6.

In this way, the left-side ear hook unit 24L has a shape with a different curvature in each portion, and is formed to cover the base of the left ear overall. By varying the curvature in portions, the adhesion of the left-side earphone unit 16L onto the left ear rises, and as a result, the brain wave measuring accuracy can be improved. Obviously, the above curvature values are merely examples, and the curvature values may be determined to match the shape of the user's ear.

Also, in a case in which the direction orthogonal to the direction in which gravity works (vertical direction) is defined as the horizontal direction, when the left-side earphone unit 16L is worn on the left ear by hooking the left-side ear hook unit 24L over the left ear, the left-side support unit 22L is disposed tilted by a predetermined angle θ from the horizontal direction. The angle θ is from 37° to 43°, for example. The angle θ may also be from 39° to 41°, and may be 40°. By adopting such an angle, the adhesion of the left-side earphone unit 16L onto the left ear can be improved.

Also, an angle φ obtained between the base portion of the first curved part 30 and the side face of the left-side support unit 22L is from 30° to 40°, for example. By setting the first curved part 30 at such an angle, the adhesion of the left-side earphone unit 16L onto the left ear can be improved.

The right-side earphone unit 16R is similar to the left-side earphone unit 16L. The right-side ear hook unit 24R includes a first curved part having the first curvature above, a second curved part having the second curvature above, and a third curved part having the third curvature above. Also, the right-side support unit 22R is disposed tilted by the angle θ described above, and the first curved part is disposed tilted by the angle φ described above.

Hereinafter, the brain wave sensor provided in the earpad constituting the left-side speaker unit 20L and the right-side speaker unit 20R will be described in detail.

Figure 6:
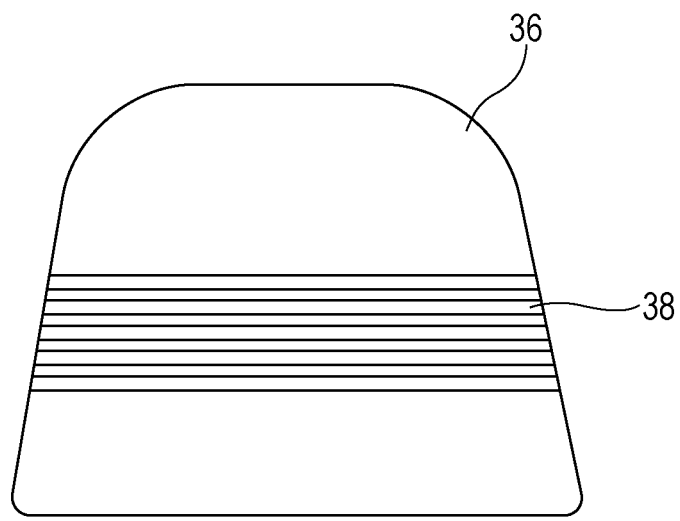
FIG. 6 is a diagram illustrating an earpad as viewed from the side.
Figure 7:
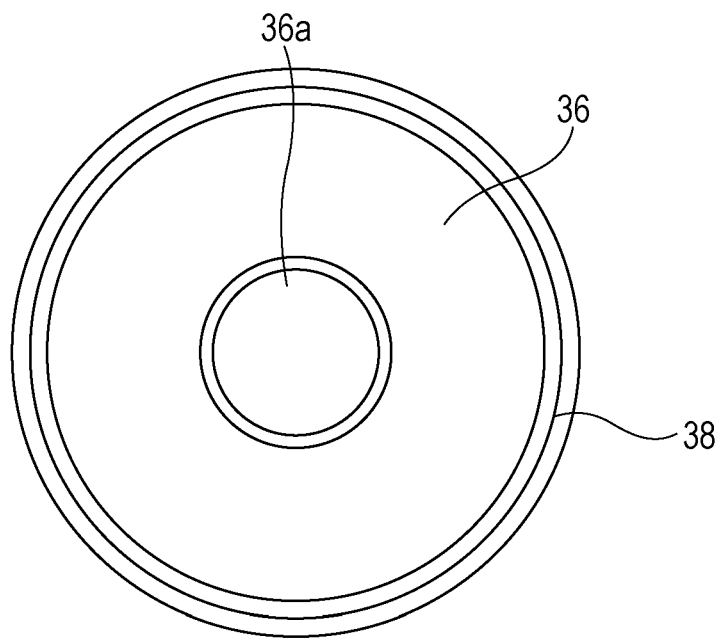
FIG. 7 is a diagram illustrating an earpad as viewed from above.

FIGS. 6 and 7 illustrate an example of an earpad. FIG. 6 is a diagram of an earpad as viewed from the side, while FIG. 7 is a diagram of an earpad as viewed from above (the side which is inserted into the ear).

An earpad 36 is used as the earpad constituting the left-side speaker unit 20L and the right-side speaker unit 20R. For the earpad 36 itself, a publicly available earpad can be used. In the example illustrated in FIGS. 6 and 7, the earpad 36 has a circular cross-section, and has a columnar shape that narrows in width (the diameter of the circle) towards the tip. A penetrating hole 36a that penetrates in the height direction is formed in the earpad 36, and sound is conveyed to the outside through this penetrating hole 36a. The earpad 36 is made of a resin such as rubber, for example.

On the side face of the earpad 36, a brain wave sensor 38 is provided as an electrode. The brain wave sensor 38 is made up of multiple linear sensors (electrodes) disposed in parallel in the height direction of the earpad 36, and disposed in the circumferential direction on the outer circumference of the earpad 36.

In the case in which the earpad 36 is provided on the left-side speaker unit 20L, the brain wave sensor 38 functions as the first left brain wave sensor 26L. Similarly, in the case in which the earpad 36 is provided on the right-side speaker unit 20R, the brain wave sensor 38 functions as the first right brain wave sensor 26R.

The brain wave sensor 38 is made up of conductive rubber made from carbon, for example. To lower the electrical resistance, the brain wave sensor 38 may also include silver paste for lowering the electrical resistance.

If the brain wave sensor 38 has a certain degree of moisture, the electric potential is more easily measured in some cases. Accordingly, the surface of the brain wave sensor 38 may also be processed to retain moisture in the brain wave sensor 38. Typically, the wettability of a solid surface depends on the roughness of the solid surface. For example, according to the Wenzel equation, as the surface roughness increases, the contact angle with a hydrophilic surface becomes smaller, and the surface becomes wetted more easily (in other words, moisture is more easily retained). Accordingly, the surface of the brain wave sensor 38 may be processed to adjust the surface roughness of the brain wave sensor 38 to be a surface roughness by which is obtained a moisture allowing for easier measurement of electric potential. As another example, by introducing an oxygenated functional group onto the surface of the brain wave sensor 38 by a surface treatment using fluorine gas, hydrophilicity can be manifested at the surface of the brain wave sensor 38, and thereby the moisture of the brain wave sensor 38 may be retained. Obviously, the moisture of the brain wave sensor 38 may also be maintained at a moisture allowing for easier measurement of electric potential by methods other than the above.

Figure 8:
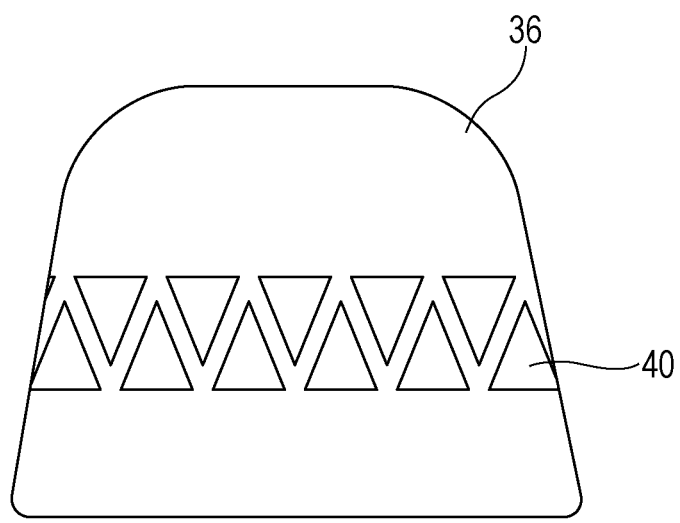
FIG. 8 is a diagram illustrating an earpad as viewed from the side.
Figure 9:
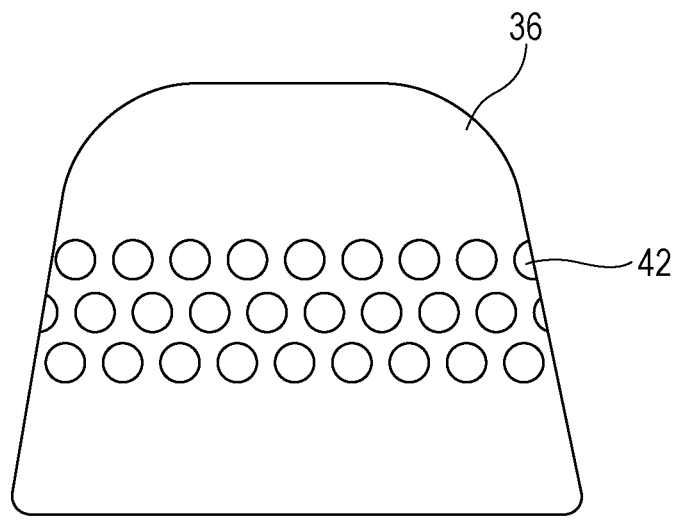
FIG. 9 is a diagram illustrating an earpad as viewed from the side.

FIGS. 8 and 9 illustrate other examples of a brain wave sensor. FIGS. 8 and 9 are diagrams illustrating the earpad 36 as viewed from the side. The earpad 36 itself has the same shape as the earpad 36 illustrated in FIGS. 6 and 7. In the example illustrated in FIG. 8, a brain wave sensor 40 that acts as an electrode is configured by multiple triangular sensors (electrodes), which are disposed in the circumferential direction on the outer circumference of the earpad 36. In the example illustrated in FIG. 9, a brain wave sensor 42 that acts as an electrode is configured by multiple circular sensors (electrodes), which are disposed in the circumferential direction on the outer circumference of the earpad 36.

Figure 10:
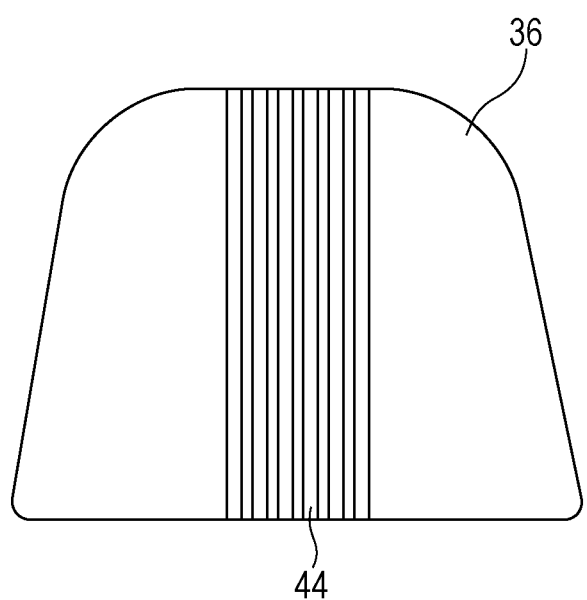
FIG. 10 is a diagram illustrating an earpad as viewed from the side.
Figure 11:
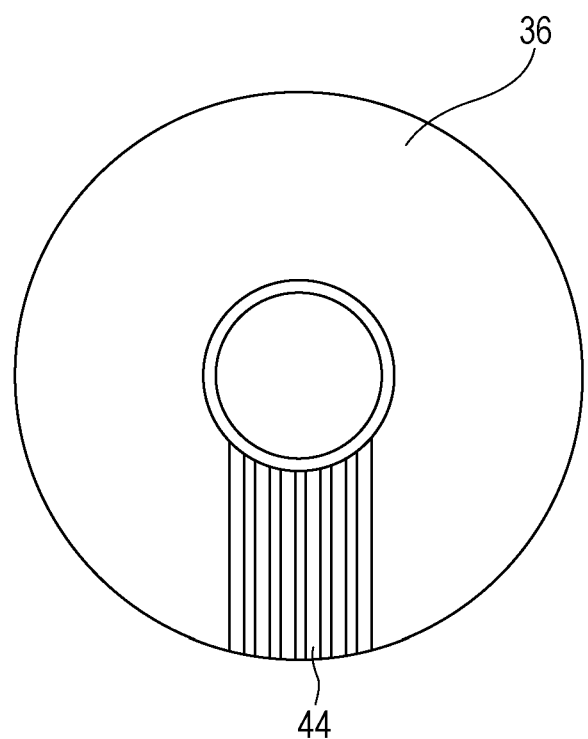
FIG. 11 is a diagram illustrating an earpad as viewed from above.
Figure 12:
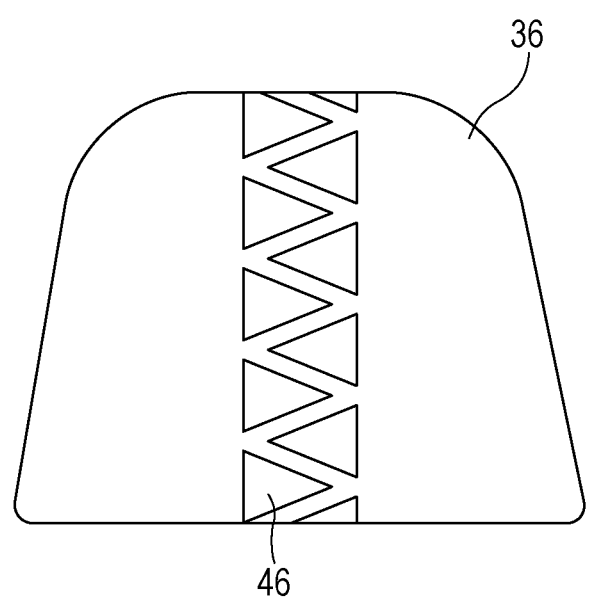
FIG. 12 is a diagram illustrating an earpad as viewed from the side.
Figure 13:
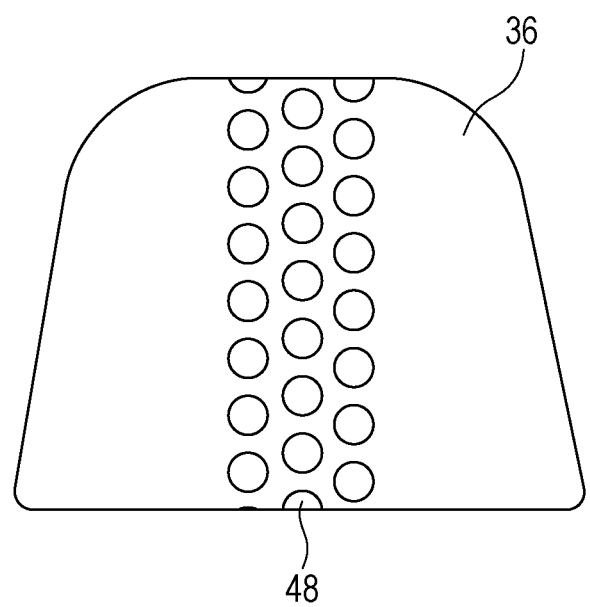
FIG. 13 is a diagram illustrating an earpad as viewed from the side.

FIGS. 10 to 13 illustrate other examples of a brain wave sensor. FIGS. 10, 12, and 13 are diagrams of the earpad 36 as viewed from the side, while FIG. 11 is a diagram of the earpad 36 as viewed from above (the side which is inserted into the ear). The earpad 36 itself has the same shape as the earpad 36 illustrated in FIGS. 6 and 7. In the examples illustrated in FIGS. 10 and 11, a brain wave sensor 44 that acts as an electrode is configured by multiple linear sensors (electrodes) disposed in parallel to the circumferential direction of the earpad 36, which are disposed in the height direction on the outer circumference of the earpad 36. In the example illustrated in FIG. 12, a brain wave sensor 46 that acts as an electrode is configured by multiple triangular sensors (electrodes), which are disposed in the height direction on the outer circumference of the earpad 36. In the example illustrated in FIG. 13, a brain wave sensor 48 that acts as an electrode is configured by multiple circular sensors (electrodes), which are disposed in the height direction on the outer circumference of the earpad 36.

The shapes and arrangements of the brain wave sensors described above are merely examples, and other shapes and arrangements may also be adopted. In addition, a brain wave sensor may also be provided over the entire circumferential face of the earpad 36.

Hereinafter, other exemplary installations of brain wave sensors will be described with reference to FIGS. 14 to 17. FIGS. 14 to 17 are perspective views illustrating a configuration of part of the earphone device 10.

Figure 14:
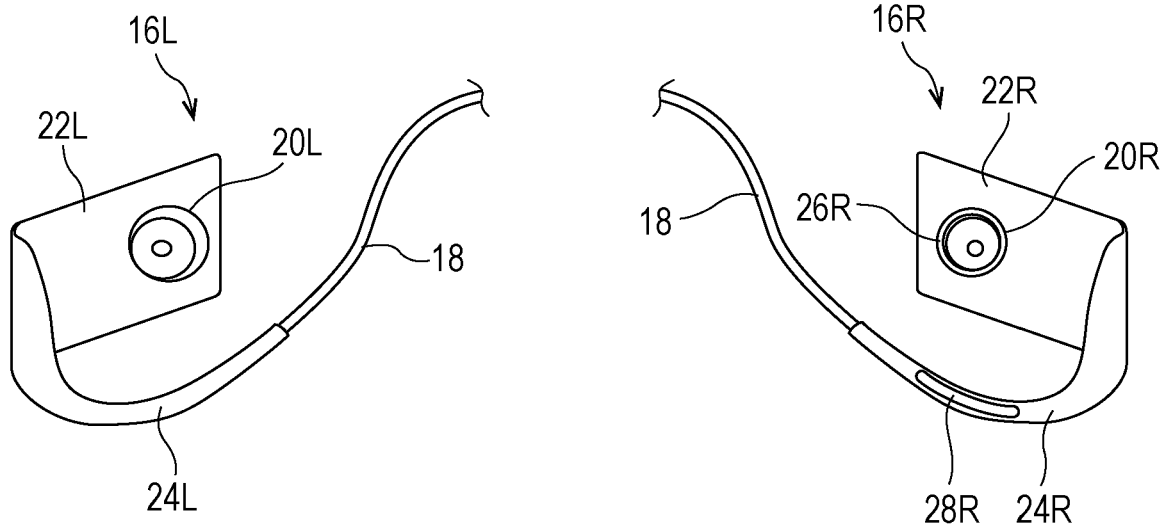
FIG. 14 is a perspective view illustrating a configuration of part of an earphone device.

In the example illustrated in FIG. 14, brain wave sensors (electrodes) are provided on the right-side earphone unit 16R, whereas brain wave sensors (electrodes) are not provided on the left-side earphone unit 16L. Namely, the first right brain wave sensor 26R is provided on the side face of the right-side speaker unit 20R (the side face of the earpad), and the second right brain wave sensor 28R is provided on the right-side ear hook unit 24R. In this case, electric potential is measured by the first right brain wave sensor 26R and the second right brain wave sensor 28R provided on the right-side earphone unit 16R, and information indicating the measurement result is transmitted from the earphone device 10 to the terminal device 12 as information indicating a brain wave measurement result. Note that brain wave sensors may also be provided on the left-side earphone unit 16L, and brain wave sensors may also not be provided on the right-side earphone unit 16R.

Figure 15:
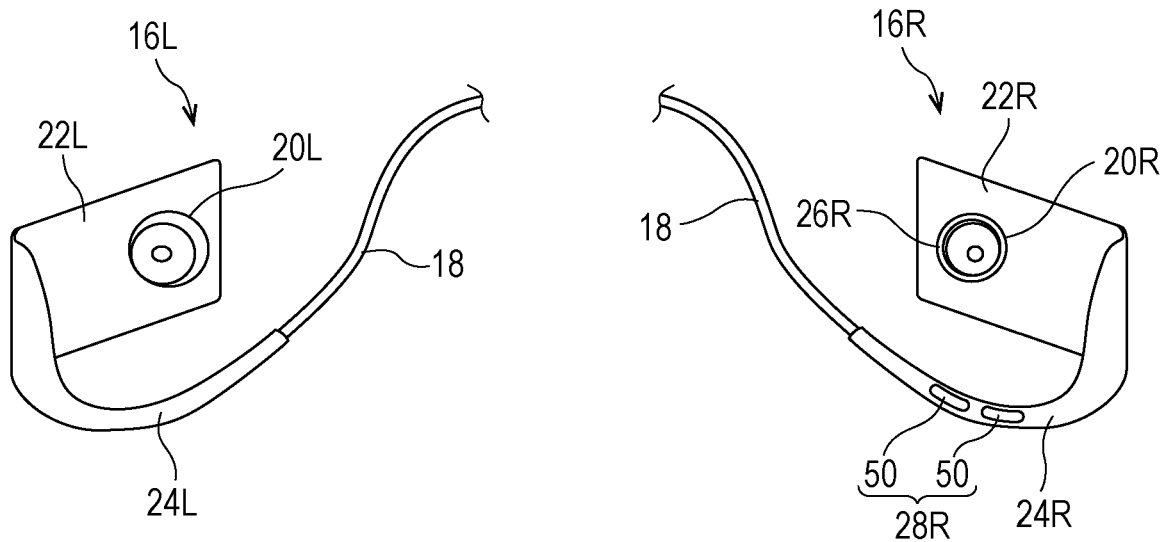
FIG. 15 is a perspective view illustrating a configuration of part of an earphone device.

In the example illustrated in FIG. 15, similarly to the example illustrated in FIG. 14, brain wave sensors (electrodes) are provided on the right-side earphone unit 16R, whereas brain wave sensors (electrodes) are not provided on the left-side earphone unit 16L. The second right brain wave sensor 28R provided on the right-side ear hook unit 24R of the right-side earphone unit 16R is a sensor that includes two brain wave sensors 50 (electrodes) provided along the right-side ear hook unit 24R. In this case, for example, the potential difference between either one of the two brain wave sensors 50 and the first right brain wave sensor 26R is adopted as the potential difference measured by the right-side earphone unit 16R. Obviously, the second right brain wave sensor 28R may also include three or more brain wave sensors 50. By configuring the second right brain wave sensor 28R with multiple brain wave sensors 50, the second right brain wave sensor 28R contacts the right ear more easily, and the electric potential is measured more reliably by the second right brain wave sensor 28R. In other words, since the electric potential is measured by having any one of the multiple brain wave sensors 50 contact the right ear, the electric potential is measured more reliably compared to the case of using only one brain wave sensor.

Figure 16:
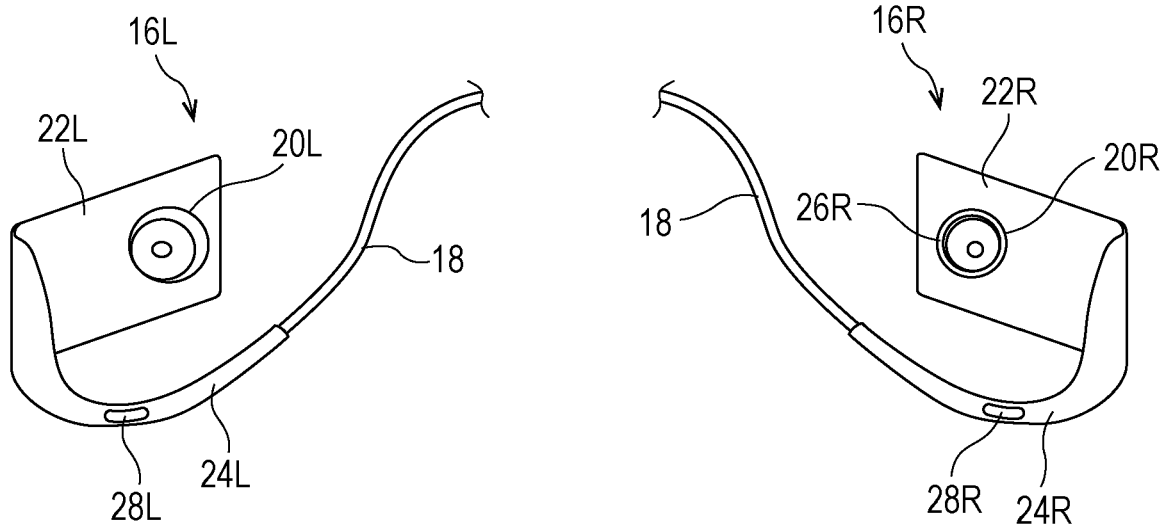
FIG. 16 is a perspective view illustrating a configuration of part of an earphone device.

In the example illustrated in FIG. 16, the first right brain wave sensor 26R is provided on the side face of the right-side speaker unit 20R (the side face of the earpad), the second right brain wave sensor 28R is provided on the right-side ear hook unit 24R, and the second left brain wave sensor 28L is provided on the left-side ear hook unit 24L. The first left brain wave sensor 26L is not provided. In this case, for example, the potential difference between the first right brain wave sensor 26R and the second right brain wave sensor 28R, or the potential difference between the first right brain wave sensor 26R and the second left brain wave sensor 28L, is measured, and the measured potential difference is adopted as the brain wave measurement result. By using the second left brain wave sensor 28L and the second right brain wave sensor 28R in this way, brain wave measurement becomes possible even in the case in which any one of the brain wave sensors is not in contact with an ear, or in which the contact between one of the brain wave sensors and an ear is unfavorable.

Figure 17:
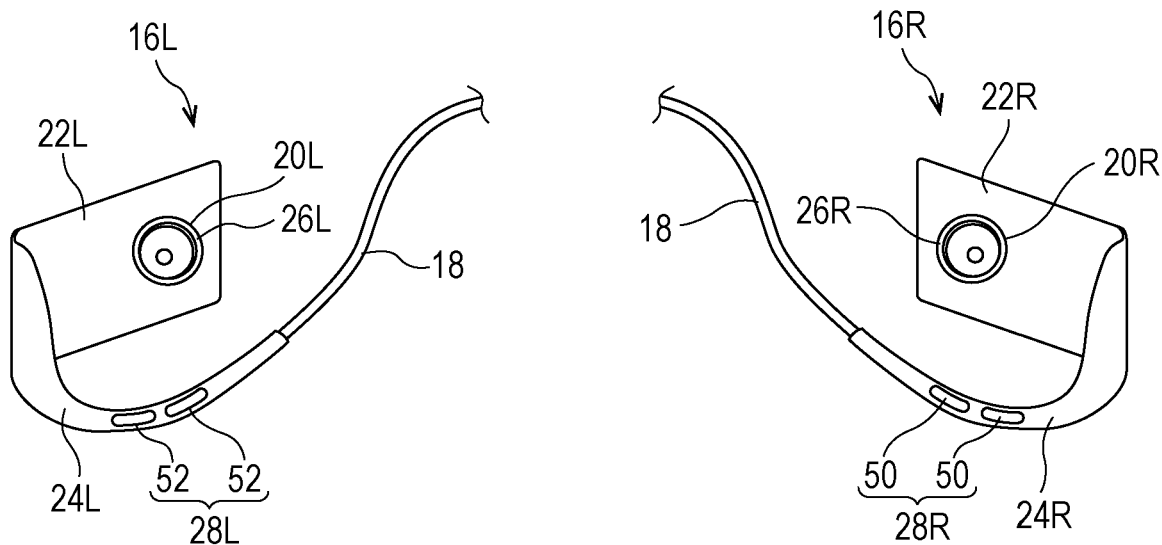
FIG. 17 is a perspective view illustrating a configuration of part of an earphone device.

In the example illustrated in FIG. 17, the first right brain wave sensor 26R is provided on the side face of the right-side speaker unit 20R (the side face of the earpad), the right-side ear hook unit 24R is provided on the right-side ear hook unit 24R, the first left brain wave sensor 26L is provided on the side face of the left-side speaker unit 20L (the side face of the earpad), and the second left brain wave sensor 28L is provided on the left-side ear hook unit 24L. Similarly to the example illustrated in FIG. 15, the second right brain wave sensor 28R is a sensor that includes two brain wave sensors 50 (electrodes) provided along the right-side ear hook unit 24R. Similarly, the second left brain wave sensor 28L is a sensor that includes two brain wave sensors 52 (electrodes) provided along the left-side ear hook unit 24L. In this case, for example, the potential difference between either of the two brain wave sensors 50 and the first right brain wave sensor 26R is adopted as the potential difference measured by the right-side earphone unit 16R, while the potential difference between either of the two brain wave sensors 52 and the first left brain wave sensor 26L is adopted as the potential difference measured by the left-side earphone unit 16L. Obviously, three or more of the brain wave sensors 50 and 52 may also be provided. By configuring the second right brain wave sensor 28R and the second left brain wave sensor 28L with multiple sensors in this way, the second right brain wave sensor 28R contacts the right ear more easily and the second left brain wave sensor 28L contacts the left ear more easily, and thus the electric potential is measured more reliably by the second right brain wave sensor 28R and the second left brain wave sensor 28L.

With the earphone device 10 according to the present exemplary embodiment, by pinching the ears with multiple brain wave sensors, the brain wave sensors can be brought into close contact with the ears, thereby improving the electric potential measurement accuracy, and as a result, the brain wave measuring accuracy can be improved.

Figure 18:
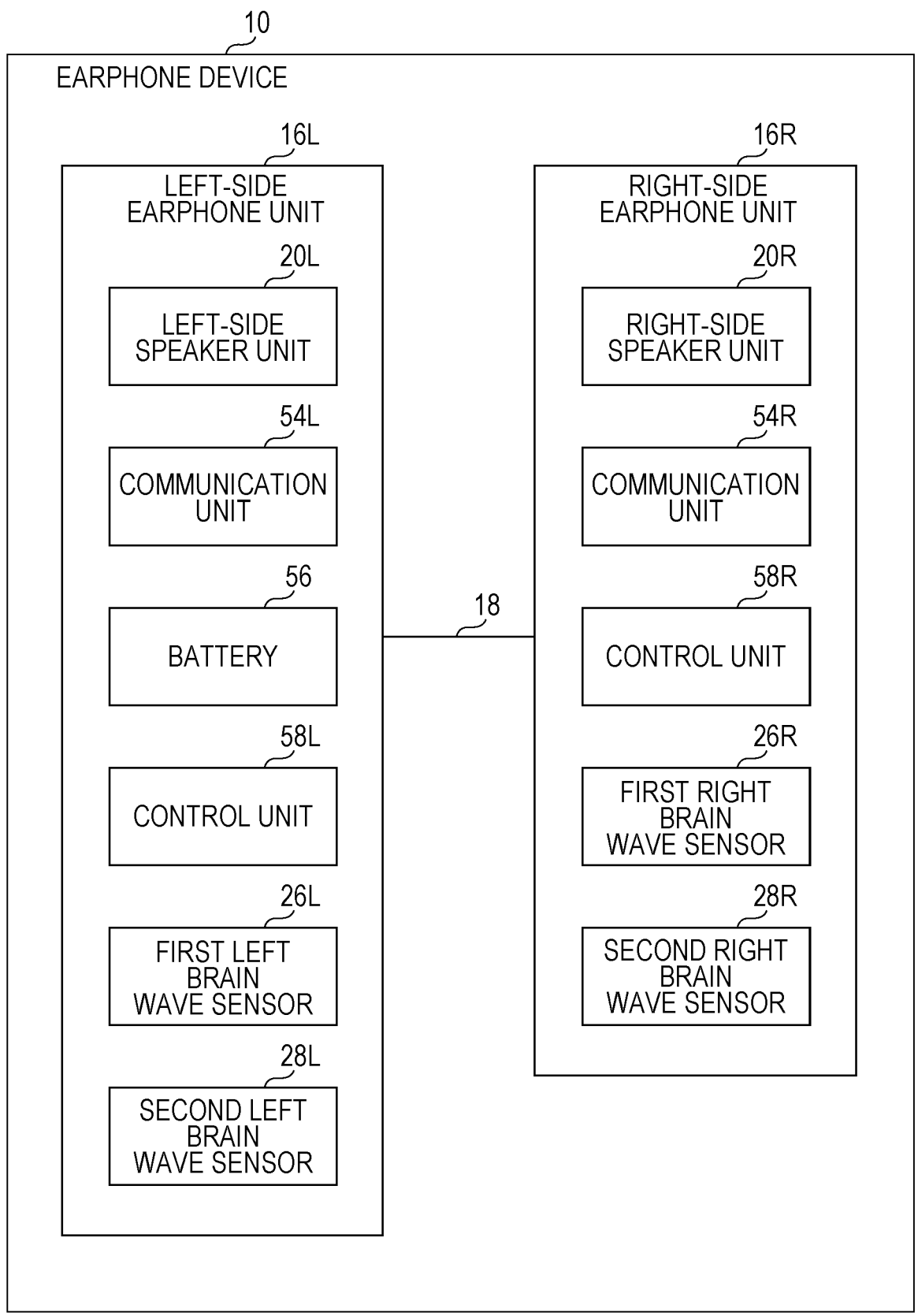
FIG. 18 is a function block diagram of an earphone device.

Hereinafter, the functions of the earphone device 10 will be described in detail with reference to FIG. 18. FIG. 18 is a function block diagram of the earphone device 10.

As described above, the earphone device 10 includes a left-side earphone unit 16L, a right-side earphone unit 16R, and a cable 18 that connects the left-side earphone unit 16L and the right-side earphone unit 16R.

The left-side earphone unit 16L includes a left-side speaker unit 20L, a first left brain wave sensor 26L, a second left brain wave sensor 28L, a communication unit 54L, a battery 56, and a control unit 58L.

The communication unit 54L is a communication interface (communication chip), and includes a function of transmitting data to other devices, and a function of receiving data from other devices. The communication unit 54L includes a wireless communication function, for example. For the communication scheme, as described earlier, short-range wireless communication such as Bluetooth, infrared communication, visible light communication, Wi-Fi communication, or the like is used. Herein, short-range wireless communication (for example, Bluetooth) is taken to be used as an example. For example, by short-range wireless communication, the communication unit 54L receives from an external device (for example, the terminal device 12) a signal expressing sound to be emitted from the left-side speaker unit 20L. The left-side speaker unit 20L produces sound in accordance with the signal received by the communication unit 54L. Additionally, by short-range wireless communication, the communication unit 54L may also transmit information indicating a brain wave measurement result to an external device (for example, the terminal device 12). Note that since the earphone device 10 may also be used in combination with external devices other than the terminal device 12 (such as a playback device or a display device, for example), the earphone device 10 may also communicate with external devices other than the terminal device 12 to receive a sound signal from such an external device, or to transmit information indicating a brain wave measurement result to such an external device.

The battery 56 supplies electric power to each unit of the left-side earphone unit 16L. For example, electric power is supplied from the battery 56 to the left-side speaker unit 20L, the communication unit 54L, and the control unit 58L, and the left-side speaker unit 20L, the communication unit 54L, and the control unit 58L are driven by the electric power supplied from the battery 56. Also, as described later, in the case in which a battery is not provided in the right-side earphone unit 16R, electric power is supplied from the battery 56 to each unit of the right-side earphone unit 16R through the cable 18. For the battery 56, a rechargeable battery is used, for example. Obviously, a non-rechargeable battery may also be used as the battery 56. Note that a shield member (anti-electromagnetic wave member) may also be provided around the battery 56 and charging-related components. By providing a shield member, noise arising from electromagnetic waves produced during charging can be reduced, and the accuracy of brain wave measurement can be raised.

The control unit 58L controls the operation of each unit of the left-side earphone unit 16L. For example, the control unit 58L controls communication by the communication unit 54L, performs processing (for example, statistical processing) on brain wave measurement results, senses a fault in each unit of the left-side earphone unit 16L, and senses a fault in the cable 18.

The right-side earphone unit 16R includes a right-side speaker unit 20R, a first right brain wave sensor 26R, a second right brain wave sensor 28R, a communication unit 54R, and a control unit 58R.

The communication unit 54R, similarly to the communication unit 54L, is a communication interface (communication chip), and includes a function of transmitting data to other devices, and a function of receiving data from other devices. The communication unit 54R includes a wireless communication function, for example. The communication scheme is the same as the communication scheme adopted by the communication unit 54L (for example, Bluetooth). For example, by short-range wireless communication, the communication unit 54R receives from the terminal device 12 a signal expressing sound to be emitted from the right-side speaker unit 20R. The right-side speaker unit 20R produces sound in accordance with the signal received by the communication unit 54R. Additionally, by short-range wireless communication, the communication unit 54R may also transmit information indicating a brain wave measurement result to the terminal device 12.

The control unit 58R controls the operation of each unit of the right-side earphone unit 16R. For example, the control unit 58R controls communication by the communication unit 54R, performs processing (for example, statistical processing) on brain wave measurement results, senses a fault in each unit of the right-side earphone unit 16R, and senses a fault in the cable 18.

Note that one of either the control unit 58L or the control unit 58R may be provided in the earphone device 10, and the one control unit may control the operation of each unit of the earphone device 10.

A battery is not provided in the right-side earphone unit 16R. As described above, electric power is supplied from the battery 56 provided in the left-side earphone unit 16L to the right-side earphone unit 16R, and the right-side speaker unit 20R, the communication unit 54R, and the control unit 58R are driven by the electric power supplied from the battery 56. By providing a battery in only one of the earphone units, the overall weight of the earphone device 10 can be reduced.

Obviously, batteries may also be provided in both the left-side earphone unit 16L and the right-side earphone unit 16R. In this case, electric power is supplied from the battery installed in the right-side earphone unit 16R to each unit of the right-side earphone unit 16R. As another example, a battery may be provided in the right-side earphone unit 16R without providing a battery in the left-side earphone unit 16L. In this case, electric power is supplied from the battery installed in the right-side earphone unit 16R to the left-side earphone unit 16L through the cable 18.

When a first potential difference is measured by the first left brain wave sensor 26L and the second left brain wave sensor 28L, and a second potential difference is measured by the first right brain wave sensor 26R and the second right brain wave sensor 28R, the control unit 58L or the control unit 58R applies statistical processing (for example, the simple average or a weighted average) to the first potential difference and the second potential difference, and adopts the value obtained by the statistical processing as a brain wave measurement result. In this case, information indicating the brain wave measurement result is transmitted by the communication unit 54L or the communication unit 54R from the earphone device 10 to the terminal device 12. Obviously, information before the statistical processing is performed may also be transmitted from the earphone device 10 to the terminal device 12, and the statistical processing may be conducted by the terminal device 12. In this case, information indicating the first potential difference is transmitted as information indicating a first brain wave measurement result by the communication unit 54L from the earphone device 10 to the terminal device 12, while information indicating the second potential difference is transmitted as information indicating a second brain wave measurement result by the communication unit 54R from the earphone device 10 to the terminal device 12.

In a case in which a fault occurs in the cable 18, information indicating the first brain wave measurement result may be transmitted by the communication unit 54L from the earphone device 10 to the terminal device 12, while information indicating the second brain wave measurement result may be transmitted by the communication unit 54R from the earphone device 10 to the terminal device 12.

In the case in which one of either the communication unit 54L or the communication unit 54R fails, the non-faulty communication unit (communication chip) may be used to transmit information indicating a brain wave measurement result to the terminal device 12.

In a case in which one of either the left-side earphone unit 16L or the right-side earphone unit 16R fails, the non-faulty earphone unit may transmit information indicating a brain wave measurement result obtained by that earphone unit to the terminal device 12.

During the charging of the battery 56, the control unit 58L or the control unit 58R may not transmit information indicating a brain wave measurement result to the terminal device 12, or stop brain wave measurement. As another example, during the charging of the battery 56, the control unit 58L may stop brain wave measurement by the first left brain wave sensor 26L and the second left brain wave sensor 28L, while the control unit 58R may continue brain wave measurement by the first right brain wave sensor 26R and the second right brain wave sensor 28R. In this case, information indicating a brain wave measurement result obtained by the right-side earphone unit 16R is transmitted from the earphone device 10 to the terminal device 12. During the charging of the battery 56, the brain wave measurement result obtained by the left-side earphone unit 16L provided with the battery 56 is more susceptible to the influence of noise arising from the charging, but the brain wave measurement result obtained by the right-side earphone unit 16R not provided with a battery is less susceptible to the influence of such noise. Consequently, by stopping brain wave measurement by the left-side earphone unit 16L and transmitting information indicating the brain wave measurement result obtained by the right-side earphone unit 16R to the terminal device 12, a brain wave measurement result that is less influenced by noise arising from charging is given to the terminal device 12. Obviously, brain wave measurement by the left-side earphone unit 16L may also be continued even during the charging of the battery 56. In this case, brain waves are obtained using the measurement result obtained by the right-side earphone unit 16R, without using the measurement result obtained by the left-side earphone unit 16L. For example, information indicating the measurement result obtained by the left-side earphone unit 16L may not be transmitted from the earphone device 10 to the terminal device 12, or may not be used during brain wave analysis.

Figure 19:
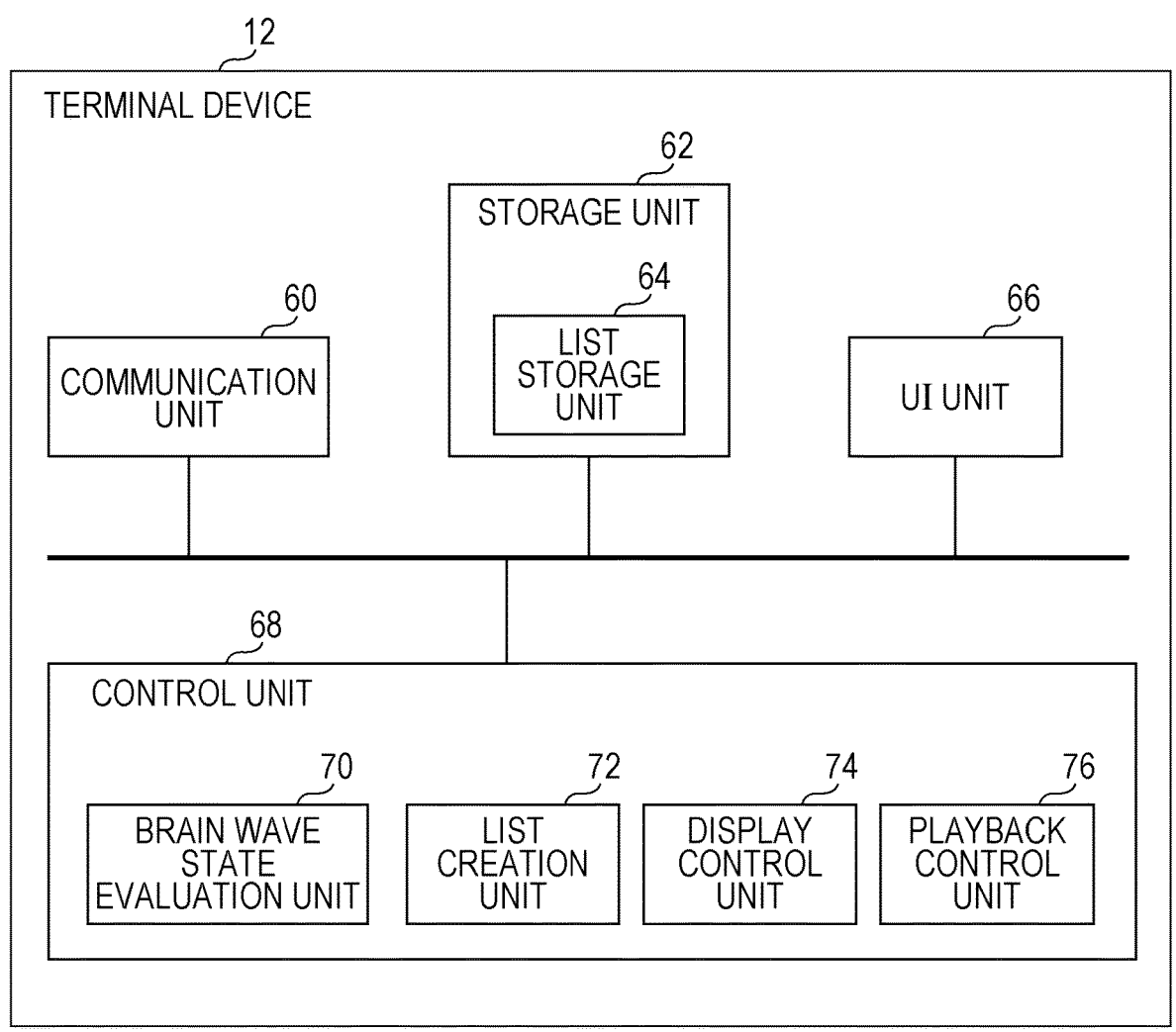
FIG. 19 is a function block diagram of a terminal device.

Hereinafter, a configuration of the terminal device 12 will be described in detail with reference to FIG. 19. FIG. 19 is a function block diagram of the terminal device 12.

The communication unit 60 is a communication interface, and includes a function of transmitting data to other devices, and a function of receiving data from other devices. The communication unit 60 includes a wireless communication function, for example. For the communication scheme, short-range wireless communication such as Bluetooth, infrared communication, visible light communication, Wi-Fi communication, or the like is used. The communication unit 60 may also include a wired communication function.

The communication unit 60 communicates with the earphone device 10 by short-range wireless communication (for example, Bluetooth), for example. Described more specifically, by short-range wireless communication, the communication unit 60 transmits a signal expressing sound to be emitted from the left-side speaker unit 20L to the communication unit 54L of the left-side speaker unit 20L, and transmits a signal expressing sound to be emitted from the right-side speaker unit 20R to the communication unit 54R of the right-side speaker unit 20R. Additionally, by short-range wireless communication, the communication unit 60 receives information indicating a brain wave measurement result from the earphone device 10. Note that the terminal device 12 may also be used in combination with earphones or a brain wave measuring device other than the earphone device 10. In this case, the terminal device 12 may receive information indicating a brain wave measurement result from such a brain wave measuring device, and transmit sound signals to the earphone device 10 or other earphones.

In addition, the communication unit 60 communicates with other devices via the communication link N by a wireless communication function such as Wi-Fi, or by a wired communication function. The communication unit 60 transmits and receives information over the Internet, for example. Via the communication link N, the communication unit 60 may download music data or receive music data in a streaming format from the music delivery server 14.

The storage unit 62 is a storage device such as a hard disk or memory (such as an SSD, for example). The storage unit 62 stores various data, various programs, address information indicating the address of the music delivery server 14, and the like, for example. Also, the storage unit 62 includes a list storage unit 64.

The list storage unit 64 stores the data of one or multiple content playlists. The content is music or video, for example, and a content playlist is a list made up of content identification information for identifying content. One or multiple pieces of content are registered in a content playlist, and the content playlist is made up of the one or multiple pieces of content identification information corresponding to the one or multiple pieces of content.

As one example of content playlists, the list storage unit 64 stores the data of one or multiple music playlists. A music playlist is a list made up of music identification information (such as a song title, an artist name, and an album name, for example) for identifying a piece of music (song). One or multiple pieces of music are registered in a music playlist, and the music playlist is made up of the one or multiple pieces of music identification information corresponding to the one or multiple pieces of music. Music playlists are created by each user, for example, and are managed in association with the user. Specifically, user identification information (such as a user ID or a user name, for example) for identifying a user is associated with the data of a music playlist. Additionally, a default music playlist may be created in advance, music playlists for individual brain wave states may be created in advance, and music playlists for individual brain wave states desired by the user may be created in advance. The data of these music playlists may be stored in the list storage unit 64. The default music playlist is a list made up of one or multiple pieces of music identification information corresponding to one or multiple preselected pieces of music (songs). Obviously, individual lists for different genres, individual lists for different artists, lists by time era, and the like may also be created. The music data itself may be stored in the storage unit 62 or in another device (such as the music delivery server 14 or another server, for example).

As one example of content playlists, the list storage unit 64 may store the data of one or multiple video playlists. A video playlist is a list made up of video identification information (such as a video title and a video creator, for example) for identifying a video. One or multiple videos are registered in a video playlist, and the video playlist is made up of the one or multiple pieces of video identification information corresponding to the one or multiple videos. Video playlists are created by each user, for example, and are managed in association with the user. Specifically, user identification information is associated with the data of a video playlist. Additionally, a default video playlist may be created in advance, and video playlists for individual brain wave states may be created in advance. The data of these video playlists may be stored in the list storage unit 64. The default video playlist is a list made up of one or multiple pieces of video identification information corresponding to one or multiple preselected videos. Obviously, individual lists for different genres, individual lists for different video creators, lists by time era, and the like may also be created. The video data itself may be stored in the storage unit 62 or in another device (such as a video delivery server or another server, for example).

Note that a content playlist containing a mix of music and video may also be created and stored in the list storage unit 64.

The UI unit 66 is a user interface, and includes a display unit and an operating unit. The display unit is a display device such as a liquid crystal display, for example. The operating unit is an input device such as a touch panel, one or more buttons, a keyboard, or a mouse, for example. Obviously, a user interface combining a display unit and an operating unit (for example, a touchscreen display, or a device that displays a keyboard or the like electronically on a display) is also acceptable.

The control unit 68 controls the operation of each unit of the terminal device 12. Additionally, the control unit 68 includes a brain wave state evaluation unit 70, a list creation unit 72, a display control unit 74, and a playback control unit 76.

The brain wave state evaluation unit 70 receives information indicating a brain wave measurement result, and by analyzing the brain wave measurement result (for example, the potential difference), evaluates the user's brain wave state. The brain wave state is a state such as concentration, relaxation, sleepiness, or alertness, for example. The brain wave state evaluation unit 70 may also quantify the brain wave state obtained by brain wave analysis. In some cases, the user's brain wave state is not confined to a single state, and instead is a mixture of multiple brain wave states. For example, if the brain wave state is a mixture of the "concentration" state and the "relaxation" state, the brain wave state evaluation unit 70 quantifies each of the "degree of concentration" and the "degree of relaxation". Note that publicly available technologies can be used as the method of evaluating a brain wave state from a brain wave measurement result (information indicating a potential difference). For example, a brain wave state can be evaluated by analyzing sigma waves, theta waves, alpha waves, and beta waves obtained from a brain wave measurement result.

The brain wave state evaluation unit 70 may compute a numerical value expressing a brain wave state per a time unit (for example, every 1 second), or compute an average value (time average) of numerical values expressing a brain wave state over a predetermined time period. Additionally, the brain wave state evaluation unit 70 may also generate a waveform expressing the change over time of the numerical value (a waveform expressing the change over time of the brain wave state).

In addition, the brain wave state evaluation unit 70 associates content with the brain wave state. For example, during the playback of music, the brain wave state evaluation unit 70 evaluates the user's brain wave state on the basis of information indicating a brain wave measurement result, and associates that music with that brain wave state. To obtain the change over time of the brain wave state, the brain wave state is measured at individual time points during a single song. With this arrangement, the brain wave state at individual time points during a song can be specified.

The brain wave state evaluation unit 70 associates music identification information (such as a title, for example) identifying a piece of music with brain wave state information indicating the user's brain wave state, for example. The music identification information is stored in the storage unit 62 in association with brain wave state information. The brain wave state information is information indicating a brain wave state obtained while the song is playing, and is information indicating numerical values expressing the brain wave state per a unit time, an average value of such numerical values, a waveform expressing change over time of such numerical values, and the like, for example. The average value is, for example, a time average over the full time period of one song, or a partial time period (for example, a specified time period). For example, in a case in which the brain wave state corresponds to "concentration", the brain wave state information includes the "degree of concentration" (a numerical value) per a unit time, the average value thereof, a waveform expressing change over time of the "degree of concentration", and the like. Additionally, in a case in which multiple brain wave states are mixed together, the brain wave state information includes numerical values expressing the respective brain wave states per a unit time, average values (time averages) of the numerical values of the respective brain wave states, waveforms expressing the respective brain wave states, and the like. For example, in a case in which "concentration" and "relaxation" are mixed together as the brain wave state, the brain wave state information includes the "degree of concentration" (a numerical value) per a unit time, the average value thereof, a waveform expressing change over time of the "degree of concentration", the "degree of relaxation" (a numerical value) per a unit time, the average value thereof, and a waveform expressing change over time of the "degree of relaxation".

The case of measuring brain waves during the playback of video is also similar to the process for music, and video identification information (such as a title, for example)

identifying a video is associated with brain wave state information indicating the user's brain wave state.

Note that a brain wave measurement result analyzed by the brain wave state evaluation unit 70 may be a result obtained by the earphone device 10, or a result obtained by another brain wave measuring device.

The brain wave state evaluation unit 70 may also be provided in another device, without being provided in the terminal device 12. For example, a management server may be included in the information processing system, and the brain wave state evaluation unit 70 may be provided in the management server. In this case, the user's brain wave state may be evaluated by another device such as the management server, and information indicating the brain wave state may be transmitted from the other device to the terminal device 12. Obviously, the brain wave state evaluation unit 70 may also be provided in the earphone device 10, whereby a brain wave measurement result is analyzed and the brain wave state is evaluated in the earphone device 10. In this case, brain wave state information indicating the evaluation may be transmitted from the earphone device 10 to the terminal device 12.

The list creation unit 72 creates a music playlist or a video playlist as a content playlist. The list creation unit 72 may create a music playlist including the music identification information of music selected by the user or a video playlist including video identification information of video selected by the user, or the list creation unit 72 may create music playlists and video playlists for individual brain wave states automatically. Obviously, the list creation unit 72 may also create individual lists for different genres, individual lists for different artists and video creators, lists by time era, and the like.

As above, in a case in which the user's brain wave state is evaluated during the playback of music, the music and the brain wave state are associated together. In this case, the list creation unit 72 creates a music playlist suited to the brain wave state (a music playlist used to achieve that brain wave state) on the basis of the brain wave state evaluation result. For example, in a case in which the average value of numerical values expressing a brain wave state associated with a certain piece of music is equal to or greater than a threshold value, the list creation unit 72 registers that piece of music in a music playlist suited to that brain wave state. For example, in a case in which the brain wave states "concentration" and "relaxation" are associated with a certain piece of music, and the "degree of concentration" is equal to or greater than a threshold value while the "degree of relaxation" is less than a threshold value, the list creation unit 72 registers the piece of music in a music playlist suited to "concentration" (a music playlist used to concentrate). In a case in which the "degree of relaxation" is also equal to or greater than the threshold value, the list creation unit 72 registers the piece of music in a music playlist related to "concentration", and also registers the piece of music in a music playlist related to "relaxation" (a music playlist used to relax). In so doing, music playlists which are unique to the user are created for individual brain wave states.

The case in which the user's brain wave state is evaluated during the playback of video is similar to the process for music, and video playlists which are unique to the user are created for individual brain wave states.

Note that the data of a content list may be created by another device (such as a PC, a smartphone, or a music player, for example) without being created by the list creation unit 72, or may be created by a device such as the music delivery server 14, a video delivery server, or a management server.

The display control unit 74 controls the display of various types of information. The display control unit 74 may cause the UI unit 66 to display information indicating a brain wave state obtained by the brain wave state evaluation unit 70 (for example, a numerical value or a waveform), may cause the UI unit 66 to display a music playlist or a video playlist, or may cause the UI unit 66 to display information related to a song or a video currently playing.

The playback control unit 76 plays back content (music and video) included in a content playlist.

For example, in a case in which the user issues a playback instruction specifying a music playlist from among multiple music playlists stored in the list storage unit 64, the playback control unit 76 plays back the music (songs) registered in the music playlist specified by the user. For example, the playback control unit 76 may acquire and play back the data of the music registered in the music playlist if such music data is stored in the storage unit 62, or the playback control unit 76 may download and play back the music data from the music delivery server 14, play back music data streamed from the music delivery server 14, or acquire and play back music data from another device other than the above. Obviously, in a case in which the user specifies a piece of music (song) itself without specifying a music playlist, the playback control unit 76 plays back the specified piece of music.

Additionally, in a case in which the user issues a playback instruction while specifying a desired brain wave state, the playback control unit 76 plays back music (songs) causing the user's brain wave state to transition to or maintain the desired brain wave state. In a case in which music and brain wave states are associated together, the playback control unit 76 plays back music associated with the user's desired brain wave state. For example, the playback control unit 76 plays back music whose numerical value (for example, average value) expressing the desired brain wave state is equal to or greater than a threshold value. To describe using a specific example, in the case in which the desired brain wave state is "concentration", the playback control unit 76 plays back music associated with a "degree of concentration" (for example, an average value) that is equal to or greater than a threshold value. The playback control unit 76 may play back music associated with a numerical value equal to or greater than a threshold value randomly, play back music having a high numerical value before music having a low numerical value, or if a genre or artist is specified, play back music which belongs to the specified genre or artist and which is associated with a numerical value equal to or greater than a threshold value. Additionally, the playback control unit 76 may also play back music registered in a music playlist suited to the desired brain wave state. For example, in a case in which the desired brain wave state is "concentration", the playback control unit 76 plays back music registered in a music playlist suited to "concentration" (a music playlist used to concentrate).

During the playback of such music, brain waves likewise are measured by the earphone device 10, the brain wave state is evaluated by the brain wave state evaluation unit 70, and the brain wave state is associated with the music. In a case of playing back music already associated with a brain wave state, the brain wave state is newly evaluated, and the new brain wave state is also associated with the music. In other words, the previously obtained brain wave state and the newly obtained brain wave state are associated with the same music. In so doing, the brain wave obtained with each playback is associated with the music as a history of the brain wave state. With this arrangement, in the case in which the user listens to the same piece of music, comparison between past brain wave states and the current brain wave state becomes possible. Obviously, the brain wave state obtained by the playback immediately preceding the current playback may be associated with the music, while brain wave states obtained even earlier may not be associated with the music. Note that in this example, brain waves are measured by the earphone device 10 during music playback, but obviously brain waves may also be measured by the earphone device 10 without playing back music or video.

In addition, the playback control unit 76 may receive music data for sample listening from the music delivery server 14, and play back the music for sample listening. The music data for sample listening is data provided free of charge, for example, in which the playback time is shorter than the playback time of fee-charging music data, and the sound quality is lower than the sound quality of fee-charging music data. During the playback of such sample music, brain waves likewise are measured by the earphone device 10, the brain wave state is evaluated by the brain wave state evaluation unit 70, and a numerical value or a waveform expressing the brain wave state is displayed on the UI unit 66. Numerical values expressing the brain wave state obtained during the playback of sample music may also be presented to the user as material for judging whether to purchase the music. As another example, a music playlist recommended by the music delivery server 14 may be displayed on the terminal device 12. Also, the music data for sample listening may be the data of one or multiple songs specified by the music delivery server 14, and may be music data selected from one or multiple genres.

In a case of playing video, a process similar to the case of playing music is conducted.

The data of a content playlist may also be stored in another device (such as the music delivery server 14, a video delivery server, or a management server, for example), without being stored in the list storage unit 64. In this case, the playback control unit 76 acquires the data of a content playlist from another device in which the data of the content playlist is stored, or references a content playlist stored in another device, and plays back content included in the content playlist.

Note that in a case of measuring a brain wave state during the playback of respective pieces of music, the playback control unit 76 plays back a part of the piece of music (song) (for example, a portion from the beginning up to partway through the song), and the brain wave state evaluation unit 70 evaluates the brain wave state on the basis of a brain wave measurement result obtained during the playback. The playback control unit 76 and the brain wave state evaluation unit 70 may treat this playback and evaluation as a set, and conduct this set (playback and evaluation) for multiple pieces of music (songs). With this arrangement, respective pieces of music are played back partially, and the brain wave state is measured during the playback of each piece of music. The list creation unit 72 may use information indicating the brain wave state obtained in this way to create music playlists for individual brain wave states. For example, by conducting the above set for multiple pieces of music in a state in which music playlists for individual brain wave states do not exist, music playlists for individual brain wave states are created easily.

The following will describe a process by the terminal device 12 in detail.

After the user puts on the earphone device 10 and the user's brain waves are measured, information indicating the brain wave measurement result is transmitted from the earphone device 10 to the terminal device 12. The brain wave state evaluation unit 70, by analyzing the information indicating a brain wave measurement result transmitted from the earphone device 10, computes a numerical value expressing the user's brain wave state, and generates a waveform expressing the change over time of the numerical value. The display control unit 74 causes the UI unit 66 to display a brain wave display screen expressing the evaluation and waveform.

Figure 20:
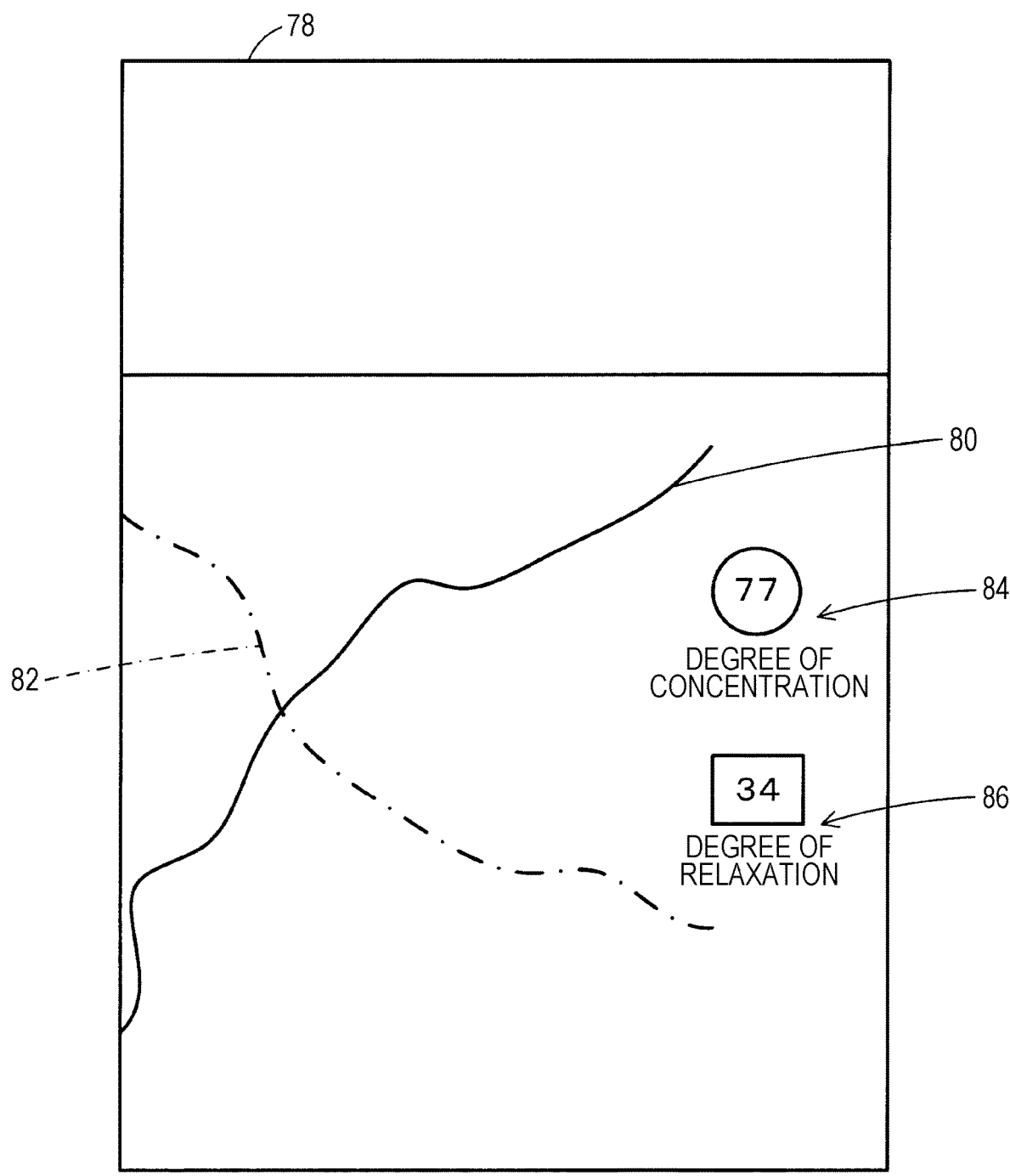
FIG. 20 is a diagram illustrating a brain wave display screen.

FIG. 20 illustrates an example of a brain wave display screen. The brain wave display screen 78 is a screen displayed on the UI unit 66. On the brain wave display screen 78, waveforms 80 and 82, and evaluation values 84 and 86 are displayed as an example. The waveform 80 is a waveform expressing change over time of the user's "degree of concentration" as an example of a brain wave state, while the waveform 82 is a waveform expressing change over time of the user's "degree of relaxation" as an example of a brain wave state. The waveforms 80 and 82 are waveforms generated by the brain wave state evaluation unit 70. The evaluation value 84 indicates a time average of the "degree of concentration" (for example, a time average over a predetermined time), while the evaluation value 86 indicates a time average of the "degree of relaxation". The evaluation values 84 and 86 are values computed by the brain wave state evaluation unit 70. In the example illustrated in FIG. 20, the brain wave state of "concentration" and the brain wave state of "relaxation" are mixed together, with each being quantified. Obviously, only information (for example, a numerical value) indicating a brain wave state specified by the user may be displayed, or only information indicating a predetermined brain wave state may be displayed.

When music is played back by the playback control unit 76, during the playback, the user's brain waves are measured by the earphone device 10, and information indicating the brain wave measurement result is transmitted from the earphone device 10 to the terminal device 12. The brain wave state evaluation unit 70 evaluates the user's brain wave state on the basis of the information indicating a brain wave measurement result. The display control unit 74 causes the UI unit 66 to display a music playback screen that displays the music selected for playback, and to display information indicating an evaluation result of the brain wave state on the music playback screen.

Figure 21:
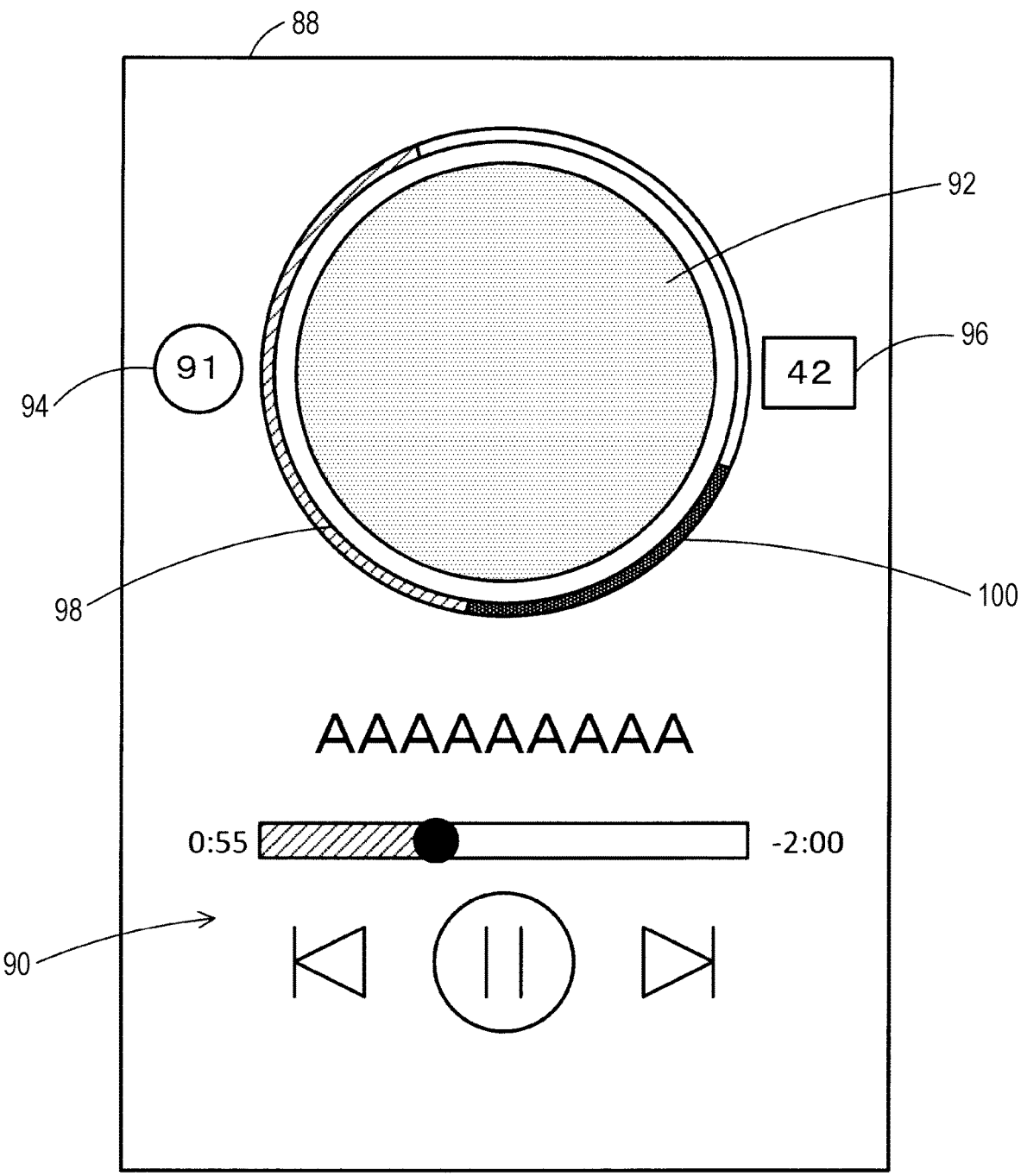
FIG. 21 is a diagram illustrating a music playback screen.

FIG. 21 illustrates an example of a music playback screen. The music playback screen 88 is a screen displayed on the UI unit 66. On the music playback screen 88, as an example, elements such as playback operation button images, a seek bar, the elapsed time, and the song title "AAAAAAAA" are displayed, as indicated by the arrow 90. Also, on the music playback screen 88, an image 92 associated with the music being played back, evaluation values 94 and 96, and arc-shaped evaluation bars 98 and 100 are displayed. The data of the image 92 may be stored in the terminal device 12, or stored in another device such as the music delivery server 14. The evaluation value 94 is a value indicating the user's "degree of concentration", while the evaluation value 96 is a value indicating the user's "degree of relaxation". The evaluation values 94 and 96 may be instantaneous values at the current time, or average values from the time of the start of playback of the song currently being played back up to the current time. The evaluation bar 98 is an image expressing the "degree of concentration". The length of the evaluation bar 98 is a length that reflects the value of the "degree of concentration", and as the value of the "degree of concentration" increases, the length of the evaluation bar 98 becomes longer. The evaluation bar 100 is an image expressing the "degree of relaxation". The length of the evaluation bar 100 is a length that reflects the value of the "degree of relaxation", and as the value of the "degree of relaxation" increases, the length of the evaluation bar 100 becomes longer.

The brain wave state evaluation unit 70 associates music identification information for identifying the piece of music currently being played back with brain wave state information indicating the brain wave state obtained during the playback, and stores the music identification information associated with the brain wave state information in the storage unit 62. In this way, for each piece of music that is played back, the brain wave state evaluation unit 70 stores the music identification information and the brain wave state information in association with each other in the storage unit 62. The list creation unit 72 creates a music playlist for individual brain wave states unique to the user, on the basis of the brain wave state information associated with the music identification information.

For example, suppose that "60" is set as a threshold value on the numerical value of a brain wave state. In the example illustrated in FIG. 21, the average value of the "degree of concentration" is "91", which is equal to or greater than the threshold value "60". Thus, the list creation unit 72 registers the music indicated in FIG. 21 in a music playlist suited to "concentration" (a music playlist used to concentrate). Note that the value of the threshold is merely one example, and another value may be used. Also, the user may also be allowed to change the threshold value.

Figure 22:
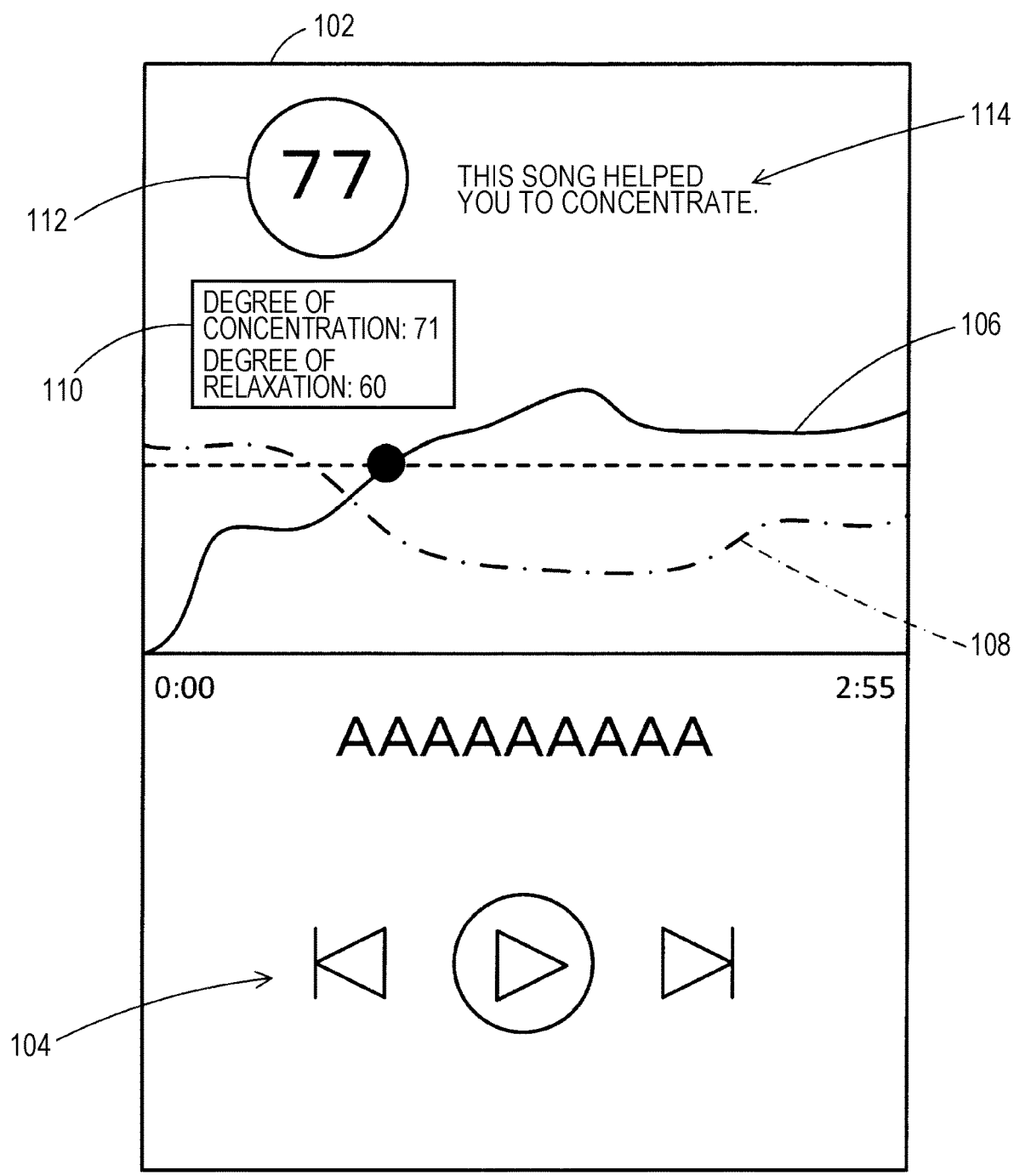
FIG. 22 is a diagram illustrating a music playback screen.

FIG. 22 illustrates another example of a music playback screen. The music playback screen 102 is a screen displayed on the UI unit 66. On the music playback screen 102, as an example, elements such as playback operation button images and the song title are displayed, as indicated by the arrow 104. In addition, on the music playback screen 102, waveforms 106 and 108, evaluation value information 110, an average value 112, and a message 114 are displayed as information indicating a brain wave state associated with the piece of music. The piece of music may be a piece of music specified by the user, or a piece of music selected randomly, for example. Also, the brain wave state is a brain wave state obtained previously, for example.

The waveform 106 is a waveform expressing change over time of the user's "degree of concentration" as an example of a brain wave state, while the waveform 108 is a waveform expressing change over time of the user's "degree of relaxation" as an example of a brain wave state. The evaluation value information 110 is information indicating the evaluation value at a specified time during the song, and indicates the "degree of concentration" and the "degree of relaxation" at that time. In the example illustrated in FIG. 22, the "degree of concentration" at that time is "71", and the "degree of relaxation" at that time is "60". Since numerical values expressing the brain wave state are obtained per a unit time, such a display is possible. If the user specifies a time during the song, the evaluation values at that time are displayed. With this arrangement, which brain states the user was in at which times during a song are presented to the user. For example, the user learns a time (that is, a part of a song) at which the user has a high "degree of concentration", and a time at which the user has a high "degree of relaxation". The average value 112 is an average of the numerical value of the brain wave state over the entire duration of one song, or a partial time. In the example illustrated in FIG. 22, the average value of the "degree of concentration" is greater than the average value of the "degree of relaxation", and thus the average value "77" of the "degree of concentration" is displayed. Also, since the average value is equal to or greater than the threshold value, the user is evaluated to have good concentration, and such a message 114 is displayed. Note that the average value of the "degree of relaxation" may also be computed and displayed.

Note that a timer function may also be provided. For example, if a desired brain wave state (such as concentration or relaxation, for example) and a length of time are specified by the user, the playback control unit 76 controls the playback of music so that the user's brain wave state is maintained in the desired brain wave state for the duration of the specified time. Multiple candidate lengths of time may be predetermined, and the user may specify a desired length of time from among the multiple candidates, or the user may specify an arbitrary desired length of time.

Figure 23:
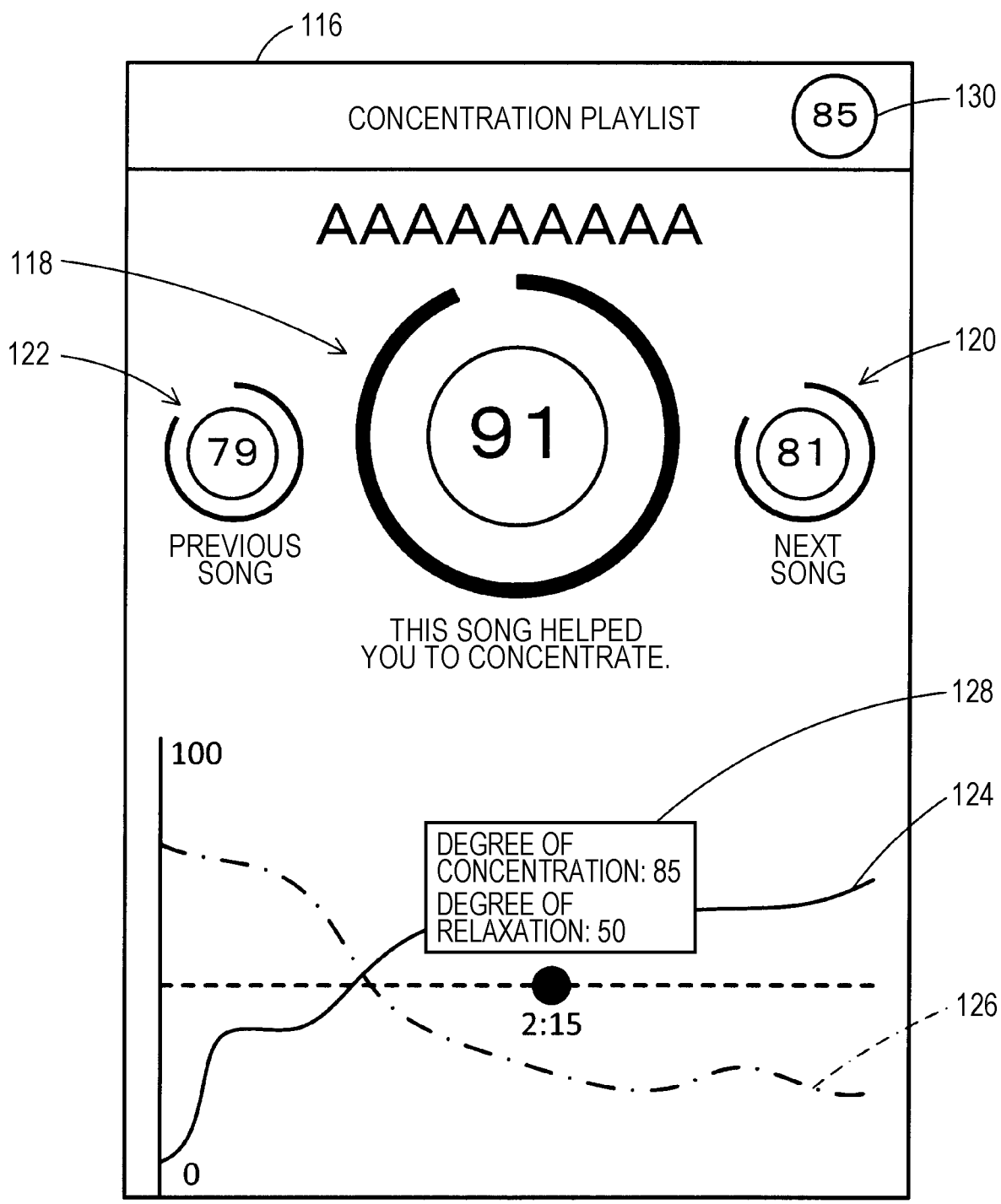
FIG. 23 is a diagram illustrating a playlist screen.

Hereinafter, a music playlist suited to a brain wave state will be described in detail with reference to FIG. 23. FIG. 23 illustrates an example of a playlist screen. The playlist screen 116 is a screen displayed on the UI unit 66. For example, if the user specifies a music playlist from among one or multiple music playlists, the display control unit 74 causes the UI unit 66 to display the playlist screen 116, and to display information related to the music included in the music playlist specified by the user on the playlist screen 116. In a case in which the user specifies a desired brain wave state, the display control unit 74 may also display information related to music included in a music playlist suited to the desired brain wave state on the playlist screen 116.

In the example illustrated in FIG. 23, information related to music registered in a music playlist suited to the "concentration" brain wave state (that is, a concentration playlist) is displayed. The concentration playlist is a list in which is registered one or multiple pieces of music associated with a "degree of concentration" equal to or greater than a threshold value.

On the playlist screen 116, an evaluation value 118 associated with the currently selected song (piece of music) in the concentration playlist, an evaluation value 120 associated with the next song, and an evaluation value 122 associated with the previous song are displayed, for example. The evaluation values 118, 120, and 122 express the "degree of concentration". For example, the degree of concentration associated with the currently selected song is "91", and a message indicating that the song has helped the user to concentrate is displayed. Also, an image having a shape corresponding to the magnitude of the degree of concentration is also displayed. Also, the title "AAAAAAAAA" of the currently selected song is displayed.

In addition, waveforms 124 and 126 as well as evaluation value information 128 are displayed. This is information indicating the brain wave states associated with the currently selected song. The waveform 124 is a waveform expressing the change over time of the "degree of concentration", while the waveform 126 is a waveform expressing the change over time of the "degree of relaxation". Also, the evaluation value information 128 is information indicating the evaluation values at a specified time during the selected song, and indicates the "degree of concentration" and the "degree of relaxation" at that time.

Additionally, a playlist evaluation value 130 is displayed. The playlist evaluation value 130 is an evaluation value of the "degree of concentration" for all songs (all pieces of music) registered in the concentration playlist, and is an average value of the numerical values (average values) of the degree of concentration for all songs, for example. In the example illustrated in FIG. 23, the playlist evaluation value 130 is "85". Note that the playlist evaluation value 130 is computed by the list creation unit 72.

Additionally, the playback control unit 76 may also play back music while changing the order of the respective pieces of music (songs) included in a music playlist, so that the user's brain wave state transitions to or maintains a desired brain wave state. For example, the playback control unit 76 plays back pieces of music from a music playlist suited to the desired brain wave state, in order of the pieces of music having the highest numerical value expressing the desired brain wave state. In the above example, the playback control unit 76 plays back songs from among all songs registered in the concentration playlist, in order of the songs having the highest "degree of concentration" evaluation value.

Figure 24:
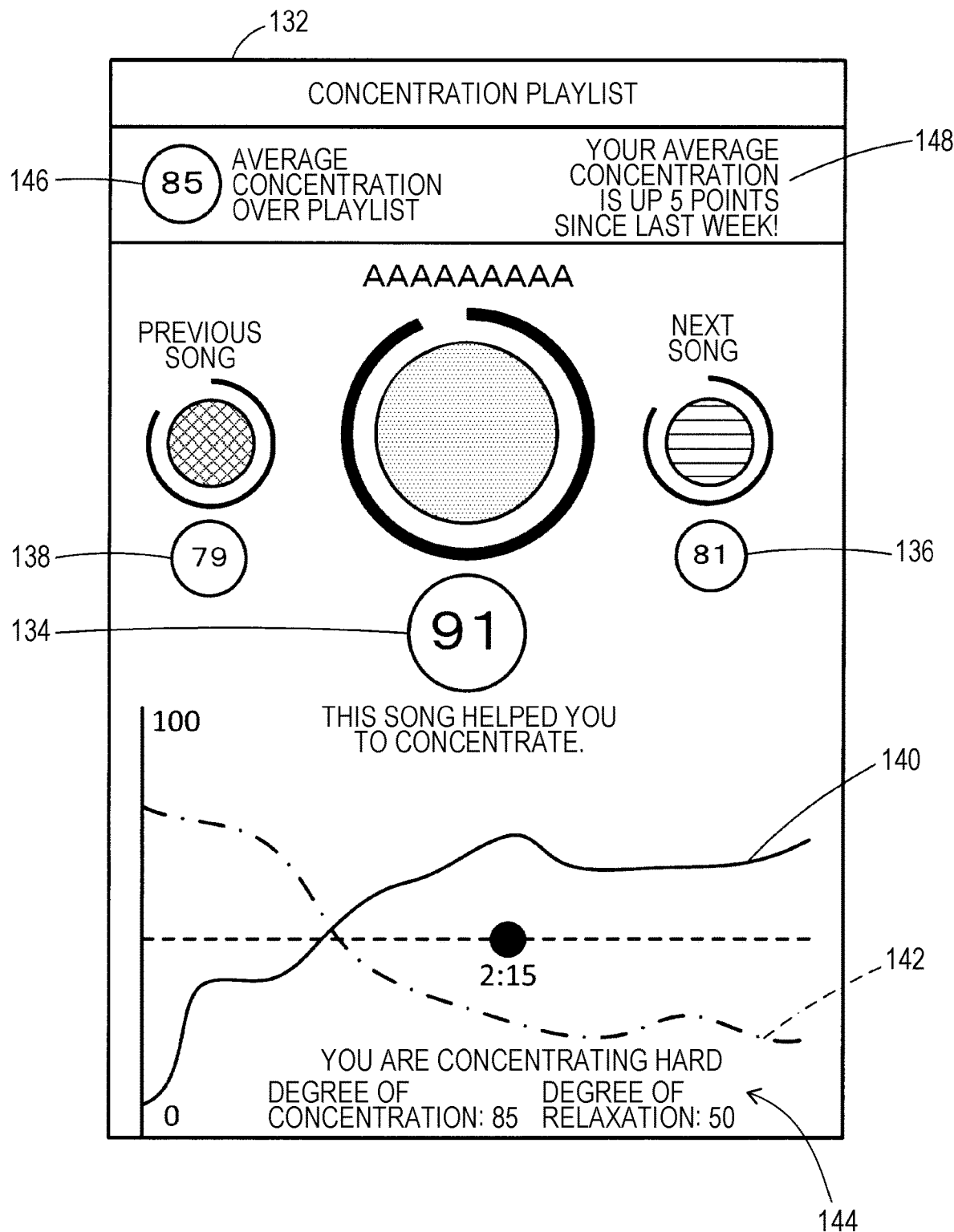
FIG. 24 is a diagram illustrating a playlist screen.

FIG. 24 illustrates another playlist screen. The playlist screen 132 is a screen displayed on the UI unit 66. On the playlist screen 132, as an example, information related to music registered in a music playlist suited to the "concentration" brain wave state (that is, a concentration playlist) is displayed.

On the playlist screen 132, an evaluation value 134 associated with the currently selected song in the concentration playlist, an evaluation value 136 associated with the next song, and an evaluation value 138 associated with the previous song are displayed, for example. The evaluation values 134, 136, and 136 express the degree of concentration. For example, the degree of concentration associated with the currently selected song is "91", and a message indicating that the song has helped the user to concentrate is displayed. In addition, an image related to the song or an image having a shape corresponding to the magnitude of the degree of concentration is also displayed. Also, the title "AAAAAAAAA" of the currently selected song is displayed.

Also, similarly to the example illustrated in FIG. 23, waveforms 140 and 142 as well as evaluation value information 144 are displayed. This is information indicating the brain wave states associated with the currently selected song. The waveform 140 is a waveform expressing the change over time of the "degree of concentration", while the waveform 142 is a waveform expressing the change over time of the "degree of relaxation". Also, the evaluation value information 144 is information indicating the evaluation values at a specified time during the selected song, and indicates the "degree of concentration" and the "degree of relaxation" at that time. Also, similarly to the example illustrated in FIG. 23, a playlist evaluation value 146 is displayed.

Additionally, comparison result information 148 is displayed. The comparison result information 148 corresponds to an example of information indicating a result of music playback with respect to the brain wave state, and is information indicating the result of a comparison between a playlist evaluation value at the current time and a playlist evaluation value at a previous time. As described above, one or multiple brain wave states obtained in the past are associated with each piece of music (song) as a history, and by using the history, the above comparison is made. The comparison is made by the list creation unit 72, for example. For example, in units of days, weeks, months, years, or a period of time specified by the user, the playlist evaluation value at the current time (such as the playlist evaluation value for today, the playlist evaluation value for this week, the playlist evaluation value for this month, or the playlist evaluation value for this year, for example) is compared to the playlist evaluation value at a previous time (such as the playlist evaluation value for yesterday, the playlist evaluation value for last week, the playlist evaluation value for last month, or the playlist evaluation value for last year, for example), and information indicating the comparison result is displayed. In the example illustrated in FIG. 24, the playlist evaluation value is up 5 points since last week. In this way, by displaying a comparison result, the user is able to learn the difference between a previous brain wave state and a current brain wave state, and utilize the system while having fun.

In addition, for each piece of music, the brain wave state evaluation unit 70 may compute the difference between a numerical value expressing the brain wave state during the previous playback and a numerical value expressing the brain wave state during the current playback, and in accordance with the difference, the list creation unit 72 may change the playback order of the respective pieces of music in a music playlist. This difference corresponds to an example of an effect of music playback on a brain wave state. For example, as the numerical value for a piece of music increases, the list creation unit 72 sets that piece of music to a higher rank in the playback order of the music playlist. For example, for multiple pieces of music included in a music playlist suited to the same brain wave state (for example, a music playlist used to concentrate), pieces of music having a greater increase in numerical value are set to higher ranks in the playback order. The display control unit 74 may also cause the UI unit 66 to display information indicating the difference obtained for each piece of music. The brain wave state evaluation unit 70 may also compute the above difference for each piece of music with respect to a brain wave state desired by the user, and the list creation unit 72 may change the playback order of the respective pieces of music in a music playlist suited to the desired brain wave state in accordance with the difference.

In addition, the brain wave state evaluation unit 70 may also compute, for each piece of music, the time taken to transition to the desired brain wave state from the beginning of listening (transition time) as an example of an effect of music playback on a brain wave state. The display control unit 74 may also cause the UI unit 66 to display information indicating the transition time for each piece of music. Also, the list creation unit 72 sets pieces of music having a shorter transition time to higher ranks in the playback order of a music playlist. For example, for multiple pieces of music included in a music playlist suited to the same brain wave state (for example, a music playlist used to concentrate), pieces of music having a shorter transition time are set to higher ranks in the playback order. With this arrangement, the pieces of music having a greater effect on the brain wave state are played back earlier, and thus compared to a case of playing back pieces of music having a lesser effect earlier, the user's brain wave state transitions to the desired brain wave state in a shorter amount of time. The brain wave state evaluation unit 70 may also compute the transition time for each piece of music with respect to a brain wave state desired by the user, and the list creation unit 72 may change the playback order of the respective pieces of music in a music playlist suited to the desired brain wave state in accordance with the transition time.

In addition, the brain wave state evaluation unit 70 may also compute, for each piece of music, the length of time that the desired brain wave state is sustained (length of sustained time) as an example of an effect of music playback on a brain wave state. The display control unit 74 may also cause the UI unit 66 to display information indicating the sustained time for each piece of music. Also, the list creation unit 72 sets pieces of music having a longer sustained time to higher ranks in the playback order of a music playlist. For example, for multiple pieces of music included in a music playlist suited to the same brain wave state (for example, a music playlist used to concentrate), pieces of music having a longer sustained time are set to higher ranks in the playback order. With this arrangement, the pieces of music having a greater effect on the brain wave state are played back earlier, and thus compared to a case of playing back pieces of music having a lesser effect earlier, the desired brain wave state is maintained more easily for a longer period of time. The brain wave state evaluation unit 70 may also compute the sustained time for each piece of music with respect to a brain wave state desired by the user, and the list creation unit 72 may change the playback order of the respective pieces of music in a music playlist suited to the desired brain wave state in accordance with the sustained time.

As described above, an effect of music playback on a brain wave state (for example, a comparison result between playlist evaluation values, or a difference between numerical values, a transition time, or a sustained time for each piece of music) is obtained. Since the music playback effect is obtained for each user, the music playback effect may be shared among multiple users, or multiple user may compete with each other in terms of the music playback effect. For example, a management server is included in the information processing system, and information indicating the music playback effect for each user is transmitted from the terminal device 12 of each user to the management server. The management server associates a ranking corresponding to the music playback effect for each user with each user, and transmits information indicating the ranking of each user to the terminal device 12 of each user. The ranking of each user is displayed on the UI unit 66 of the terminal device 12 of each user. With this arrangement, a sense of competition is produced among multiple users, and each user is able to utilize the system of the present exemplary embodiment while having fun. Additionally, information indicating the music playback effect for each user may be transmitted to the terminal device 12 of other users by either going through or not going through the management server, and may be displayed on the UI unit 66 of the terminal device 12. With this arrangement, a user is able to learn of the effects on other uses, and is able to utilize the system of the present exemplary embodiment while having fun.

In addition, information indicating the brain wave state of each user may be transmitted from the terminal device 12 of each user to a management server included in the information processing system, and the management server may manage and control the brain wave state of each user. For example, the management server may transmit, to the terminal device 12 of each user, music causing the brain wave state of each user to transition to or maintain a specific brain wave state. For example, to enable employees at a workplace to relax, the management server may transmit, to the terminal device 12 of each user, music causing the brain wave state of each employee to transition to or maintain "relaxation". At this point, the management server may also transmit different music to the respective terminal devices 12 of individual users.

According to the present exemplary embodiment, music causing the user's brain wave state to transition to or maintain a desired brain wave state is played back, and thus music enabling the user to reach a desired state can be played back. The music enabling the user to reach a desired state may be different for each user in some cases. According to the present exemplary embodiment, by evaluating the brain wave state and controlling the playback of music using the evaluation result, different music enabling individual users to reach a desired state can be played back for each users. For example, music matching each user's tastes can be played back.

(Coordination with Music Delivery Service)

Hereinafter, coordination with a music delivery service will be described in detail. The playback control unit 76 receives music data for sample listening from the music delivery server 14, and plays back the music for sample listening. At this point, brain waves likewise are measured by the earphone device 10, the brain wave state is evaluated by the brain wave state evaluation unit 70, and an evaluation result (for example, a numerical value or a waveform) is displayed. On the basis of the brain wave state during the playback of the sample music, the control unit 68 determines whether or not to add that music to the user's music playlist. The display control unit 74 causes the UI unit 66 to display information indicating the determination result. For example, in a case in which a numerical value expressing the brain wave state is a threshold value or greater, the music is determined to be a target of inclusion, and a message indicating this determination is displayed. For example, in a case in which the "degree of concentration" becomes equal to or greater than a threshold value during the playback of a certain piece of sample music, that piece of music is displayed as music suitable for concentration. In other words, that piece of music is recommended as music to use for concentration. With this arrangement, the user is provided with information which aids the user in judging whether or not to purchase music data. For example, music matching the user's tastes is presented to the user.

In addition, different sample music for individual brain wave states may be prepared in advance, the music delivery server 14 may transmit music data for sample listening which is associated with a brain wave state specified by the user to the terminal device 12, and the terminal device 12 may play back the sample music. For example, music for concentration, music for relaxation, and the like is prepared as sample music, and if the user desires "concentration" as the brain wave state, the music for concentration is played back as the sample music. During playback, if the "degree of concentration" becomes equal to or greater than a threshold value, the music that the user is currently sampling is recommended as music that raises that user's degree of concentration. The display control unit 74 causes the UI unit 66 to display information indicating the recommendation. With this arrangement, the user easily learns which pieces of music enable him or her to obtain a desired brain wave state.

Note that in the music delivery service, the price of each piece of music may also be changed in accordance with the effect of music playback on the brain wave state (for example, a comparison result between playlist evaluation values, or a difference between numerical values, a transition time, or a sustained time for each piece of music). For example, the price may be raised for music having a greater effect. For example, information indicating the effect of music playback on each user is transmitted from the terminal device 12 of each user to the music delivery server 14, and the music delivery server 14 applies statistical processing (such as a simple average or a weighted average, for example) on the effect of music playback on each user to decide the price of each piece of music in accordance with the value obtained by the application of statistical processing.

A system according to the present exemplary embodiment may coordinate with one music delivery service, or coordinate with multiple music delivery services. In the case of coordinating with multiple music delivery services, the music delivery service may be switched to enable usage of each music delivery service. Also, in a case in which multiple music delivery services are consolidated to provide a single music delivery service, the single consolidated music delivery service may be used.

In addition, the sample listening of music may be made available when the user puts on the earphone device 10 and the user's brain waves are measured. For example, listening is made available when information indicating a brain wave measurement result obtained by the measurement is transmitted from the terminal device 12 to the music delivery server 14, whereby music data for sample listening is transmitted from the music delivery server 14 to the terminal device 12, and music for sample listening is played back. With this arrangement, usage of the earphone device 10 is encouraged compared to a case in which sample listening is made available even when the earphone device 10 is not being used.

Note that the playback control unit 76 may also play back music while altering the volume of the music, arranging the music, or altering the playback speed of the music, in accordance with the user's brain wave state. Even the same song gives the user a different impression depending on the volume, arrangement, and speed, and thus the brain wave state may also change. The playback control unit 76 alters the volume of music being played back, arranges the music, or alters the playback speed so that the user's brain wave state during the music playback more closely approaches the desired brain wave state, or in other words, so that the numerical value expressing the desired brain wave state goes higher.

(Exemplary Modification 1)

Figure 25:
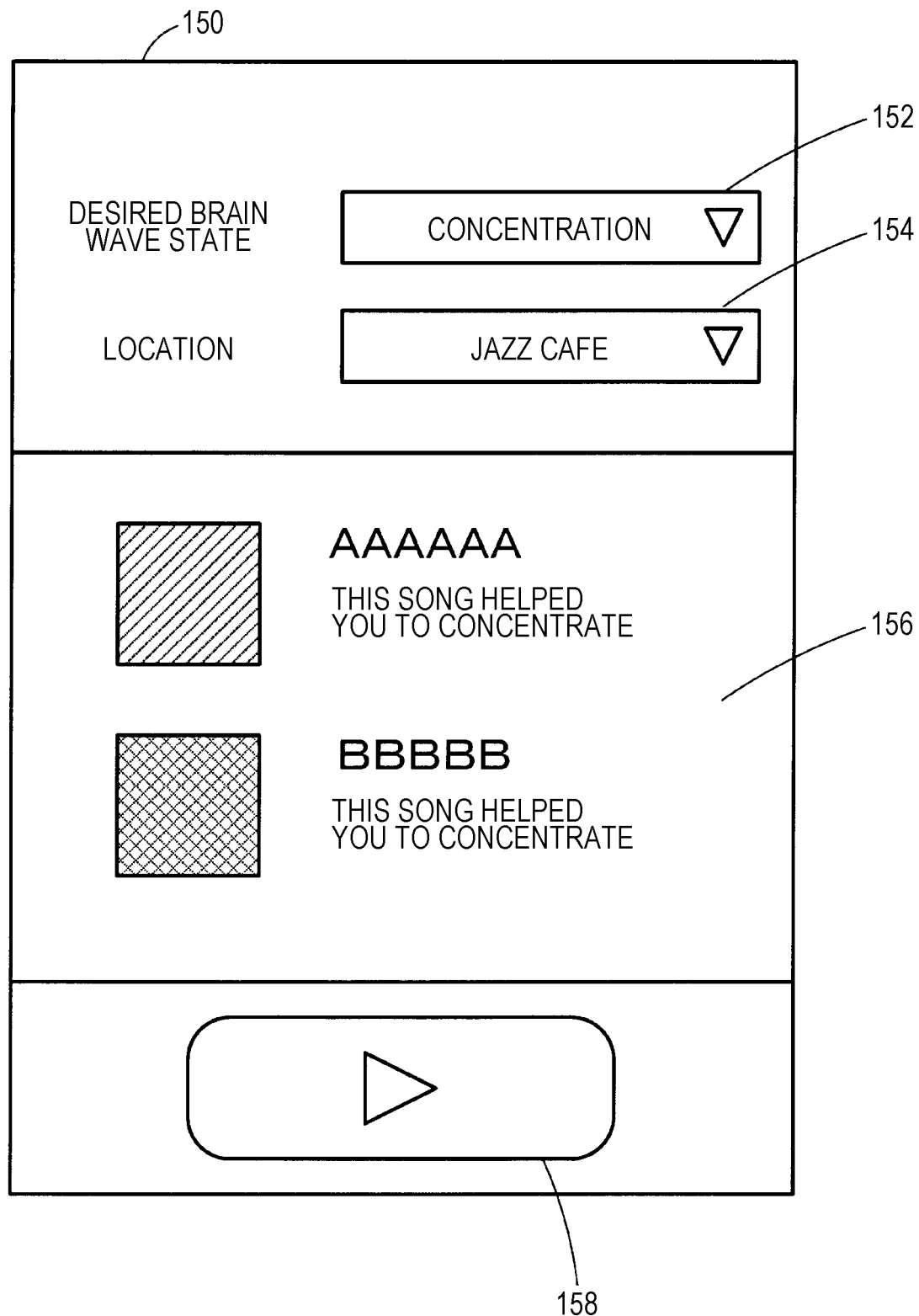
FIG. 25 is a diagram illustrating a parameter input screen.
Figure 26:
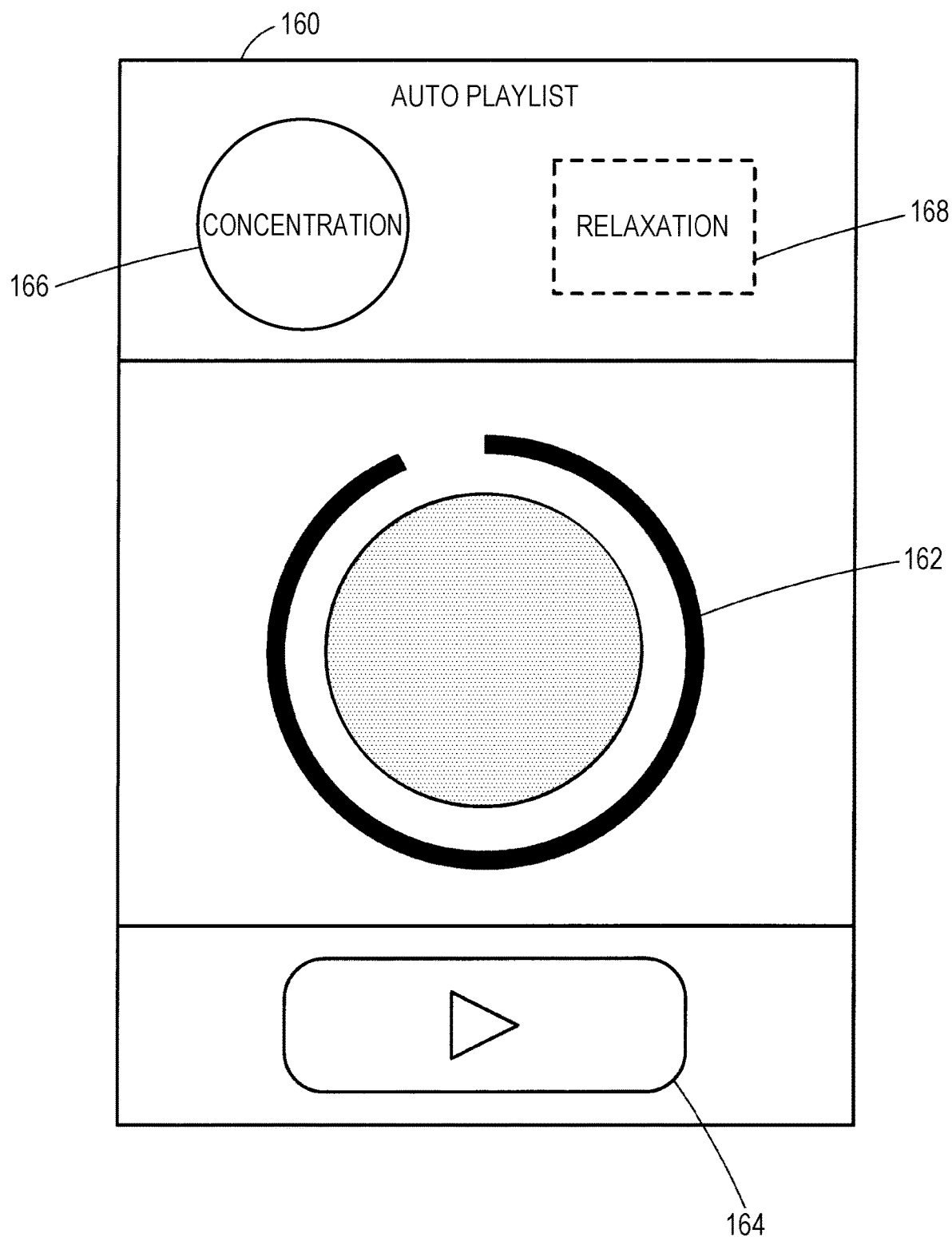
FIG. 26 is a diagram illustrating a music playback screen.

Hereinafter, Exemplary Modification 1 of a music playback list will be described with reference to FIGS. 25 and 26. FIG. 25 illustrates an example of a parameter input screen, while FIG. 26 illustrates an example of a music playback screen.

First, a parameter input screen will be described with reference to FIG. 25. The parameter input screen 150 is a screen displayed on the UI unit 66. For example, if the user issues an instruction to display the parameter input screen 150, the display control unit 74 causes the UI unit 66 to display the parameter input screen 150. On the parameter input screen 150, input fields 152 and 154 are displayed. The input field 152 is a field for inputting information indicating a "desired brain wave state", while the input field 154 is a field for inputting information indicating a "location". As an example, the input field 152 is a pull-down menu displaying a list of candidates for the "desired brain wave state", while the input field 154 is a pull-down menu displaying a list of candidates for the "location". Obviously, the user may also directly input a text string indicating a desired brain wave state and a text string indicating a location. In the example illustrated in FIG. 25, "concentration" is specified as the "desired brain wave state", and "jazz cafe" is specified as the "location". In other words, the user's desire is to "concentrate in a jazz cafe".

The display control unit 74 causes the UI unit 66 to display a music playlist including music associated with the specified desired brain wave state and location. In the example illustrated in FIG. 25, music identification information (such as song titles, for example) registered in the music playlist are displayed in a song display field 156. Hereinafter, music associated with a brain wave state and a location will be described in detail.

In the exemplary modification, a piece of music (song), a brain wave state during the playback of that piece of music, and a location where that piece of music is played back are associated with each other. As above, a brain wave state is associated with each piece of music. The location where a piece of music is played back is specified by a Global Positioning System (GPS) function, for example. For example, in a case in which the playback device (for example, the terminal device 12) is provided with a GPS function, and music is played back by the playback device, position information about the playback device during the playback is acquired by the GPS function, while in addition, a brain wave measurement result is obtained by the earphone device 10. In so doing, a piece of music, the position of the playback device playing back that piece of music, and the user's brain wave state during the playback are obtained, and the brain wave state evaluation unit 70 stores the music identification information of that piece of music, information indicating the position (position information) and the brain wave state information in association with each other in the storage unit 62. With this arrangement, when a brain wave state and a location are specified, music associated with the specified brain wave state and location, or in other words, music by which the specified brain wave state is obtained at the specified location, is determined.

The list creation unit 72 creates music playlists for individual brain wave states and individual locations, in accordance with the associations of music identification information, position information, and brain wave state information. The display control unit 74 causes the UI unit 66 to display a music playlist including music associated with the specified brain wave state and location. In the example illustrated in FIG. 25, since "concentration" is specified as the "desired brain wave state", and "jazz cafe" is specified as the "location", the display control unit 74 causes the UI unit 66 to display a music playlist including music associated with the brain wave state "concentration" and the location "jazz cafe". This music playlist may be considered a list suitable for concentrating in a jazz cafe.

Note that an initial playlist in which music, a location, and a brain wave state estimated to be obtained by playing back the music at that location are pre-associated may be precreated, and the initial music playlist may be used. In this case, the display control unit 74 causes the UI unit 66 to display the initial music playlist associated with the specified brain wave state and location.

On the parameter input screen 150, a Play button image 158 is displayed, and if the Play button image 158 is pressed by the user, the screen transitions to the music playback screen 160 illustrated in FIG. 26. The music playback screen 160 is a screen for playing back the music included in a music playlist selected as described above (for example, a music playlist suitable for concentrating in a jazz cafe). On the music playback screen 160, information 162 indicating the brain wave state associated with the song to be played back is displayed. The information 162 is an image having a shape that corresponds to a numerical value, for example. On the music playback screen 160, a Play button image 164 is displayed, and if the Play button image 164 is pressed by the user, the song to be played back is played back.

Note that button images 166 and 168 expressing brain wave states are displayed on the music playback screen 160, and if the user presses one of the button images, the display control unit 74 causes the UI unit 66 to display a music playlist for the brain wave state associated with that button image. The button image 166 is an image associated with the brain wave state "concentration", while the button image 168 is an image associated with the brain wave state "relaxation". In the examples illustrated in FIGS. 25 and 26, "concentration" is specified as the brain wave state. In this state, if the user presses the button image 168, the display control unit 74 causes the UI unit 66 to display a music playlist including music associated with the brain wave state "relaxation" and the location "jazz cafe". In so doing, the user is able to switch to a desired brain wave state.

According to Exemplary Modification 1, music causing the user's brain wave state to transition to or maintain a desired brain wave state is played back at a location specified by the user.

Note that the playback control unit 76 may also play back music suited to the user's current location by utilizing position information. For example, current position information about the terminal device 12 is acquired by the terminal device 12, and the playback control unit 76 plays back music associated with a brain wave state desired by the user, and the position. For example, music suited to desk work, music suited to work outdoors, or the like is played back.

In the example illustrated in FIG. 25, the user specifies both a desired brain wave state and a location, but the user may also specify only one of the two. In this case, the display control unit 74 causes the UI unit 66 to display a music playlist suited to that one. For example, in a case in which the user specifies a desired brain wave state, the display control unit 74 causes the UI unit 66 to display a music playlist in which is registered music associated with the desired brain wave state, whereas in a case in which the user specifies a location, the display control unit 74 causes the UI unit 66 to display a music playlist in which is registered music associated with the location.

(Exemplary Modification 2)

Figure 27:
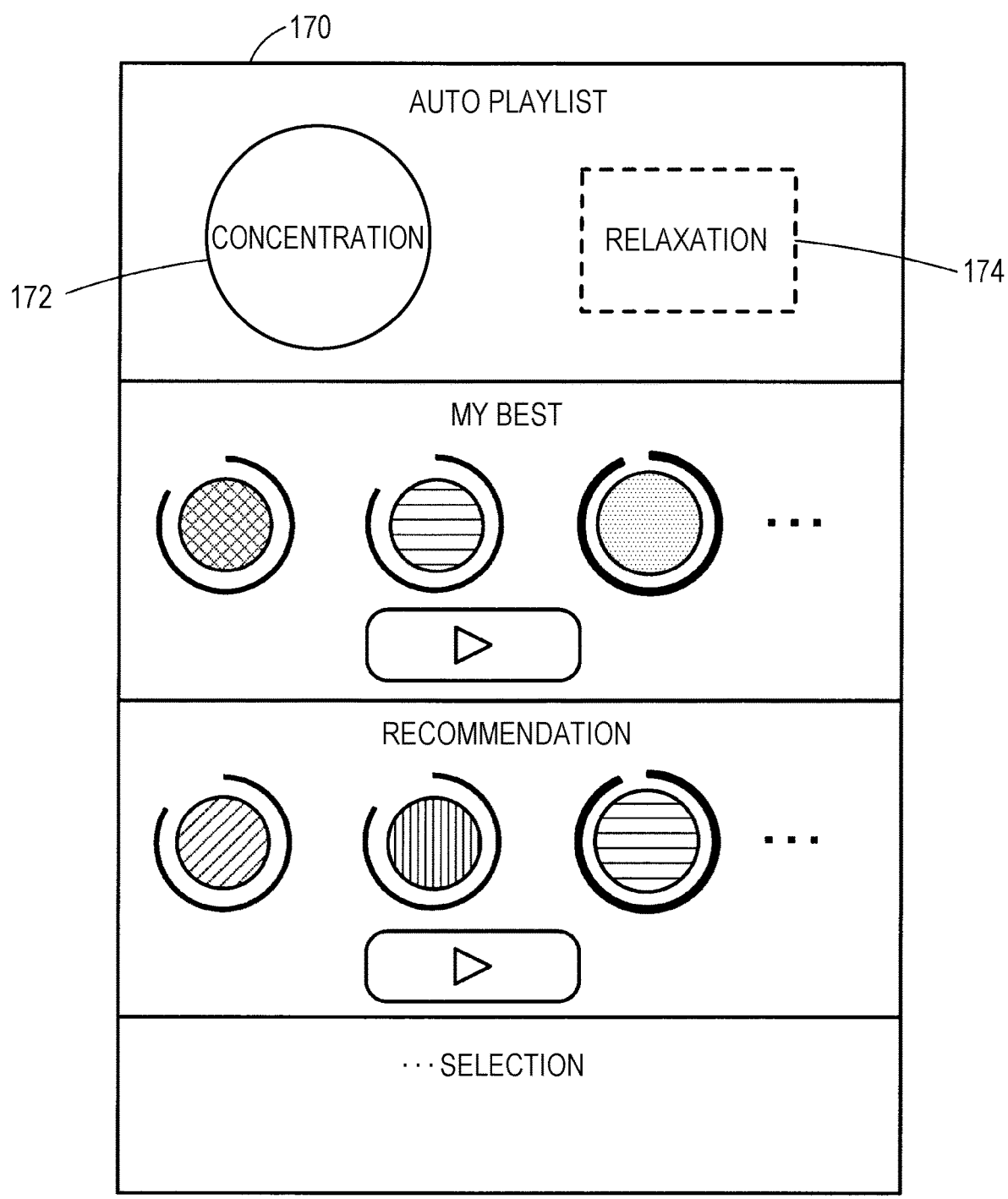
FIG. 27 is a diagram illustrating a list selection screen.

Hereinafter, Exemplary Modification 2 will be described with reference to FIG. 27. FIG. 27 illustrates an example of a list selection screen.

In Exemplary Modification 2, the music playlists of other users may also be displayed. FIG. 27 illustrates an example of such a display. If the user issues an instruction to display a music playlist, the display control unit 74 causes the UI unit 66 to display a list selection screen 170 on which music playlists are displayed. In the example illustrated in FIG. 27, a music playlist called "My Best", a music playlist called "Recommendation", and a music playlist called " . . . Selection" are displayed on the list selection screen 170. These music playlists are lists made up of pieces of music (songs) associated with the user's desired brain wave state. The "My Best" list is a list that includes music selected by the user personally. The "Recommendation" list is a list recommended by another user. The " . . . Selection" list is a list that includes music selected by users of a specific occupation, industry sector, gender, age, or the like. In addition, a list by a celebrity may be created, and such a list may be displayed.

For example, music playlists are uploaded from the terminal device 12 to the music delivery server 14 by a manual operation or automatically. With this arrangement, music playlists by respective users (such as music playlists for individual brain wave states, and music playlists including music selected personally by each user, for example) are sent to the music delivery server 14 and managed by the music delivery server 14.

For example, if a user specifies a desired brain wave state, information indicating the desired brain wave state is transmitted from the terminal device 12 to the music delivery server 14, and the music delivery server 14 transmits data indicating a music playlist suited to the desired brain wave state to the terminal device 12. As described above, the music playlist may be a music playlist recommended by another user, or the like.

If the user selects a music playlist and presses a Play button image on the list selection screen 170, the songs included in that music playlist are played back.

According to Exemplary Modification 2, music can be played back in accordance with a music playlist by another user, and thus the range of selection for music playlists becomes broader compared to the case of using only one's own music playlists.

Note that button images 172 and 174 expressing brain wave states are displayed on the list selection screen 170, and if the user presses one of the button images, the display control unit 74 causes the UI unit 66 to display a music playlist for the brain wave state associated with that button image. The button image 172 is an image associated with the brain wave state "concentration", while the button image 174 is an image associated with the brain wave state "relaxation". In the example illustrated in FIG. 27, "concentration" is specified as the brain wave state. In this state, if the user presses the button image 174, the display control unit 74 causes the UI unit 66 to display a music playlist including music associated with the brain wave state "relaxation". In so doing, the user is able to switch to a desired brain wave state.

Also, similarly to Exemplary Modification 1, in a case in which the user specifies a desired brain wave state and a location, music playlists suited to the desired brain wave state and the location may be displayed.

Other Exemplary Embodiments

Figure 28:
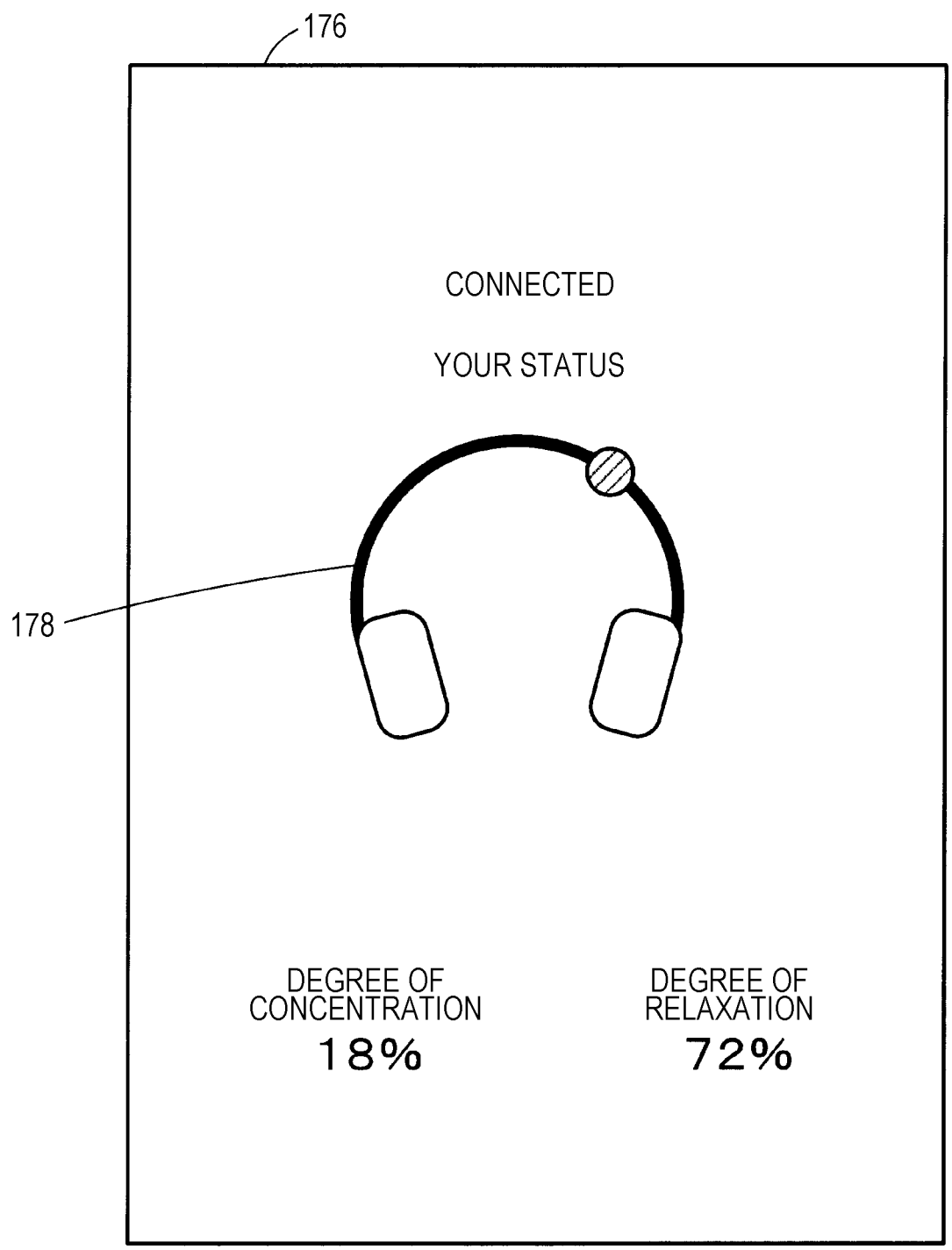
FIG. 28 is a diagram illustrating a brain wave display screen.

Hereinafter, other exemplary embodiments will be described. If the user uses the terminal device 12 to issue an instruction to connect to the earphone device 10, the terminal device 12 communicates with the earphone device 10 by short-range wireless communication (for example, Bluetooth), for example, thereby connecting the earphone device 10 and the terminal device 12 by short-range wireless communication. If the user puts on the earphone device 10, brain waves are measured by the earphone device 10. FIG. 28 illustrates an example of a brain wave display screen displayed on the UI unit 66 of the terminal device 12 at this point. On a brain wave display screen 176, an image 178 corresponding to the earphone device 10, a message indicating that the earphone device 10 is connected to the terminal device 12, a brain wave measurement result (for example, Concentration: 18% and Relaxation: 72%), and the like are displayed. In this state, if music is played back, the brain waves during the playback are measured as described earlier. At this point, the images illustrated in FIG. 21 or FIG. 22 are displayed on the UI unit 66 of the terminal device 12, for example. For example, if one or multiple pieces of music for sample listening are played back, brain wave are measured for each piece of music, and the measurement results are recorded.

Figure 29:
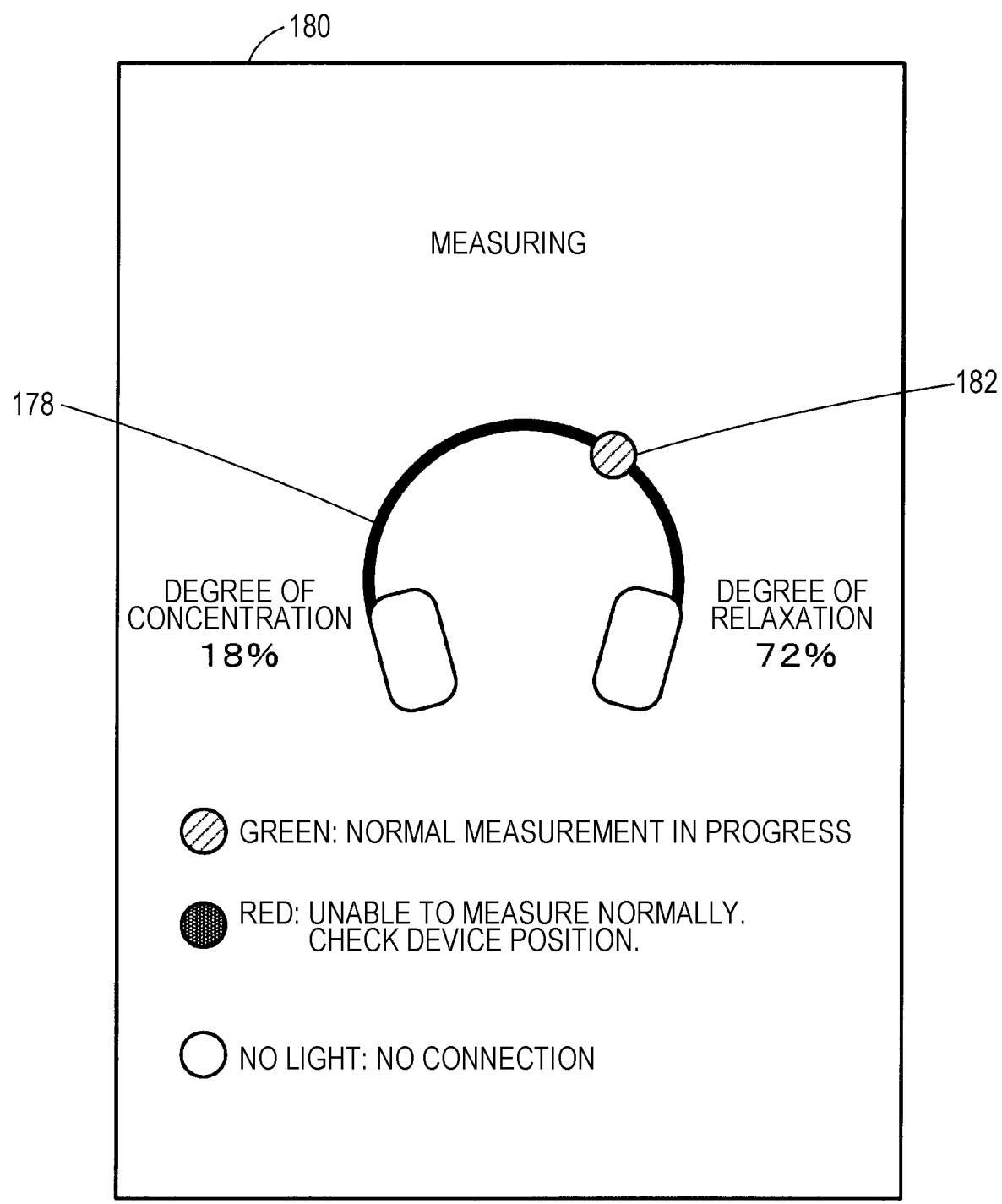
FIG. 29 is a diagram illustrating a brain wave display screen.

In addition, information indicating the brain wave measurement state may also be displayed. FIG. 29 illustrates an example of such a display. A brain wave display screen 180 is displayed on the UI unit 66 of the terminal device 12, similarly to the brain wave display screen 176 described above. On the brain wave display screen 180, an image 178 corresponding to the earphone device 10 is displayed together with a mark 182 that acts as an image expressing the brain wave measurement state. The display control unit 74 changes the display mode of the mark 182 (such as the color, shape, or size, for example) in accordance with the brain wave measurement state. In the example illustrated in FIG. 29, the color of the mark 182 changes in accordance with the brain wave measurement state. For example, in a case in which brain waves are being measured normally, the mark 182 is displayed in a green color. In a case in which brain waves are not being measured normally, the mark 182 is displayed in a red color. In a case in which the earphone device 10 is not connected to the earphone device 10 (for example, in the case of connecting by Bluetooth, when the earphone device 10 and the terminal device 12 are not paired), the mark 182 is displayed without lighting up. For example, in a case in which the potential difference returned as the brain wave measurement result corresponds to a noise level (for example, less than a threshold value), the brain waves are treated as not being measured normally, and the mark 182 is displayed in a red color. In a case in which the potential difference is equal to or greater than the threshold value, the brain waves are treated as being measured normally, and the mark 182 is displayed in a green color. In this way, by displaying information indicating the brain wave measurement state, the user is able to correct the wearing position of the earphone device 10, and as a result, the brain wave state can be measured more accurately.

Figure 30:
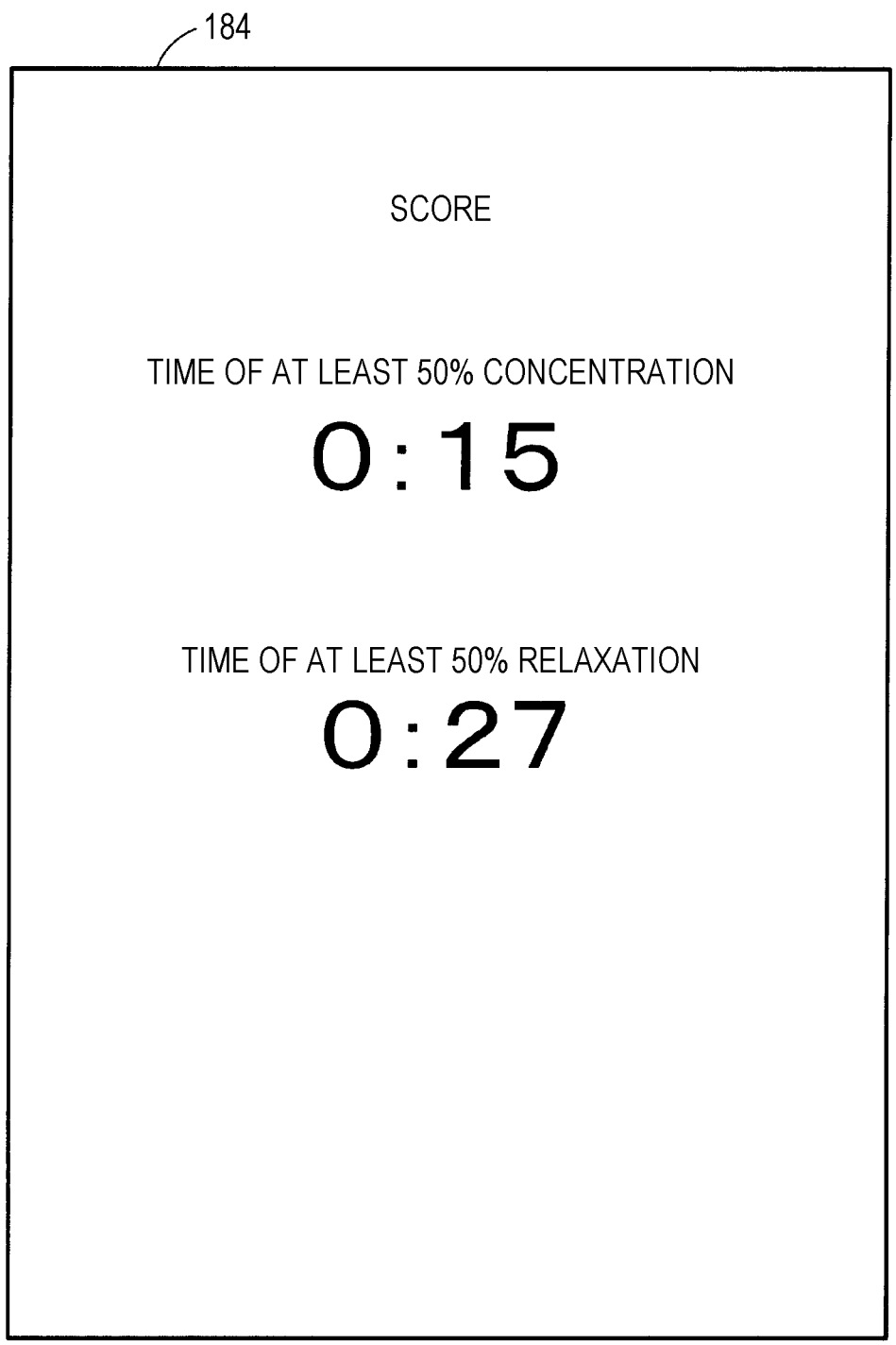
FIG. 30 is a diagram illustrating a brain wave measurement result.

FIG. 30 illustrates an example of the display of a brain wave measurement result. A measurement result screen 184 is displayed on the UI unit 66 of the terminal device 12 after or during brain wave measurement, or the like. On the measurement result screen 184, as an example, the duration over which a numerical value expressing a brain wave state stayed equal to or greater than a predetermined threshold value is indicated. The threshold value is 50% as an example. Obviously, the value is not limited to this example, and a different value may be used, or the user may set an arbitrary value. In the example illustrated in FIG. 29, the duration over which the degree of concentration stayed equal to or greater than 50% is "15 seconds", while the duration over which the degree of relaxation stayed equal to or greater than 50% is "27 seconds". These values may be results measured during the playback of music or video, or may be results measured without playing back music or video, for example.

Figure 31:
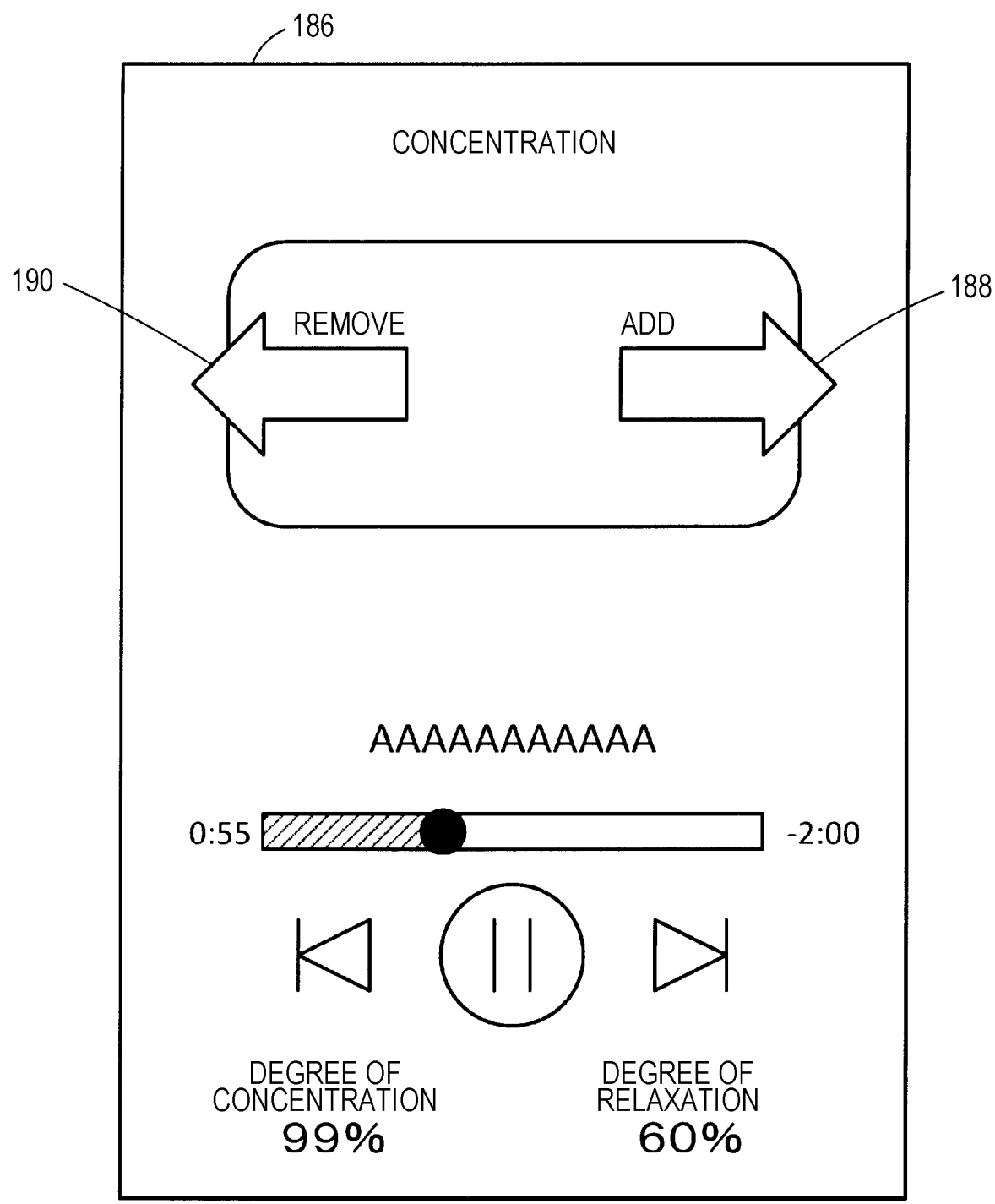
FIG. 31 is a diagram illustrating a music display screen.

Hereinafter, an example of an operation when adding music to a music playlist will be described with reference to FIG. 31. FIG. 31 illustrates an example of a music display screen. The music display screen 186 is displayed on the UI unit 66 of the terminal device 12. On the music display screen 186, information related to music specified by the user may be displayed, or information related to music selected randomly may be displayed. Additionally, images for issuing a Play instruction and the like may also be displayed. By having the user perform a so-called flick operation while a piece of music is being displayed on the music display screen 186, that piece of music is added to a music playlist or removed from a music playlist. For example, if the user rapidly moves an indicator such as a finger or stylus in the direction of an arrow 188 (a direction associated with adding to a playlist) on the music display screen 186, the piece of music currently being displayed is added to a music playlist, whereas if the user rapidly moves the indicator in the direction of an arrow 190 (a direction associated with removing from a playlist), the piece of music currently being displayed is removed from the music playlist. For example, by having the user specify a brain wave state associated with a music playlist and performing the above operations, music is added to or removed from a music playlist associated with that brain wave state. In the example illustrated in FIG. 31, "concentration" is specified as the brain wave state. If the user performs a flick operation in the direction of the arrow 188, the piece of music currently being displayed is added to a "music playlist used to concentrate", whereas if the user performs a flick operation in the direction of the arrow 190, the piece of music currently being displayed is removed from the "music playlist used to concentrate". Music is similarly added to or removed from music playlists associated with other brain wave states (for example, relaxation). With a simple operation like the above, a music playlist can be edited.

Figure 32:
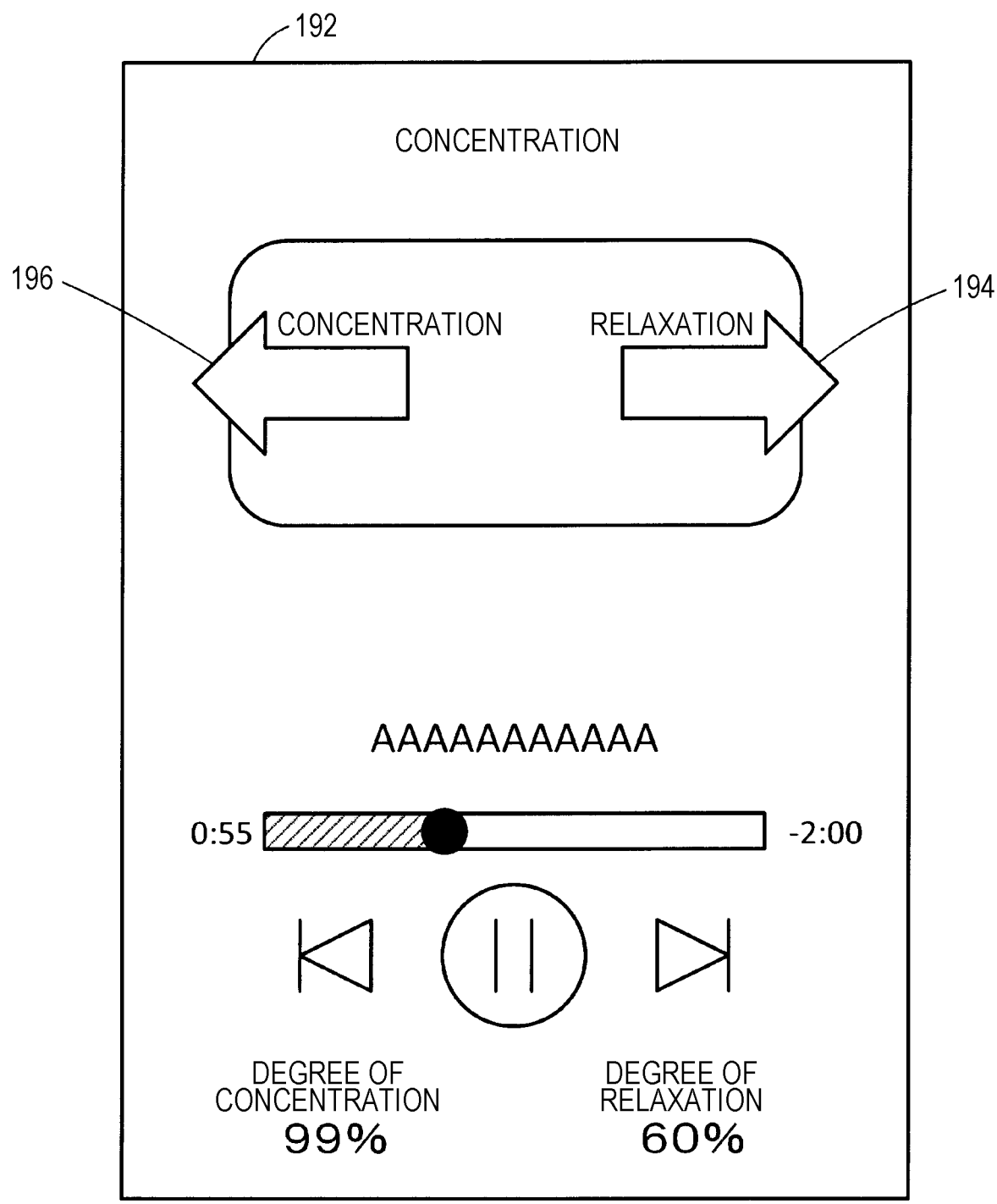
FIG. 32 is a diagram illustrating a playlist screen.

In addition, a music playlist may also be associated with a brain wave state by a flick operation like the above. Such an operation will be described with reference to FIG. 32. FIG. 32 illustrates an example of a playlist screen. The playlist screen 192 is displayed on the UI unit 66 of the terminal device 12. On the playlist screen 192, information related to a music playlist specified by the user (such as the name of the music playlist, for example) and information related to the music playlist provided by the music delivery service is displayed, for example. Additionally, images for issuing a Play instruction and the like may also be displayed. By having the user perform a flick operation while a music playlist is being displayed on the playlist screen 192, a brain wave state is associated with that music playlist. The association is conducted by the list creation unit 72. For example, if the user rapidly moves an indicator in the direction of an arrow 194 (a direction associated with relaxation) on the playlist screen 192, "relaxation" is associated as the brain wave state with the music playlist currently being displayed. In this case, the music playlist is registered as a music playlist used to relax. Also, if the user rapidly moves an indicator in the direction of an arrow 196 (a direction associated with concentration) on the playlist screen 192, "concentration" is associated as the brain wave state with the music playlist currently being displayed. In this case, the music playlist is registered as a music playlist used to concentrate. With a simple operation like the above, a brain wave state can be associated with a music playlist. Obviously, a brain wave state may also be associated with a piece of music by a similar operation. For example, in a case in which a flick operation in the direction of the arrow 194 is performed while information related to a piece of music is being displayed, "relaxation" is associated as the brain wave state with that piece of music.

The above terminal device 12 is realized by the cooperative action of hardware and software as an example. Specifically, the terminal device 12 is provided with one or multiple processors such as CPUs (not illustrated). By having the one or multiple processors load and execute a program stored in a storage device (not illustrated), the functions of the respective units of the terminal device 12 are realized. The program is stored in the storage device via a recording medium such as a CD or DVD, for example, or alternatively, via a communication link such as a network. As another example, the respective units of the terminal device 12 may be realized by hardware resources such as a processor, an electronic circuit, or an application-specific integrated circuit (ASIC), for example. A device such as memory may also be used in such a realization. As yet another example, the respective units of the terminal device 12 may also be realized by a digital signal processor (DSP), a field-programmable gate array (FPGA), or the like.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information processing system, comprising:
   a terminal device, and
   a brain wave measuring device, comprising:
      a first brain wave measuring unit that is configured to contact an ear of a user, the first brain wave measuring unit comprising a plurality of electrodes that either (i) each have a linear, elongate shape and are parallel to one another or (ii) are arranged into a plurality of rows that are each linear in shape and parallel to one another;
      a second brain wave measuring unit that comprises an electrode, is joined to the first brain wave measuring unit, and is configured to contact the ear;
      a transmitter that transmits a brain wave measurement result obtained by the first brain wave measuring unit and the second brain wave measuring unit to the terminal device; and
      a speaker unit configured to be inserted into the ear of the user, wherein
   the terminal device associates with one another each of (i) the brain wave measurement result, (ii) sounds played through the speaker unit, and (iii) a location of the user, and
   the terminal device generates a playlist for the user of sounds to be played through the speaker unit based on a location of the user input by the user and a desired brain wave state input by the user.

2. The information processing system according to claim 1, wherein
   the first brain wave measuring unit and the second brain wave measuring unit are configured to pinch the ear.

3. The information processing system according to claim 1, wherein:
   the first brain wave measuring unit is provided on an outer circumference of the speaker unit.

4. The information processing system according to claim 3, further comprising:
   an ear hook unit which is joined to a support member that supports the speaker unit and which is configured to be hooked onto the ear, wherein
   the second brain wave measuring unit is provided on the ear hook unit.

5. The information processing system according to claim 4, wherein
   the ear hook unit has a curved part that is configured to contact an underside of the ear, and
   the second brain wave measuring unit is provided on the curved part.

6. The information processing system according to claim 5, wherein
   the curved part has portions of different curvature.

7. The information processing system according to claim 6, wherein
   the curvature increases in stages along the curved part from a position close to the support member to a position farther away from the support member.

8. The information processing system according to claim 4, wherein
   the second brain wave measuring unit includes a plurality of brain wave sensors provided along the ear hook unit.

9. The information processing system according to claim 3, further comprising:
   a battery that supplies electric power for driving the speaker unit, wherein
   the transmitter stops transmission of the brain wave measurement result while the battery is charging.

10. The information processing system according to claim 9, wherein
    in a case in which an anti-electromagnetic wave member is installed, the transmitter transmits the brain wave measurement result to the terminal device even while the battery is charging.

11. The information processing system according to claim 1, wherein
    the transmitter transmits the brain wave measurement result to the terminal device by wireless communication.

12. An information processing system, comprising:
    a terminal device;
    a first brain wave measuring device, configured to be worn on a first ear of a user and to measure brain waves of the user;
    a second brain wave measuring device, configured to be worn on a second ear of the user and to measure brain waves of the user; and
    a transmitter that transmits a brain wave measurement result obtained by the first brain wave measuring device and the second brain wave measuring device to the terminal device, wherein:
    the first brain wave measuring device includes
       a first brain wave measuring unit that is configured to contact the first ear, the first brain wave measuring unit comprising a plurality of electrodes that either (i) each have a linear, elongate shape and are parallel to one another or (ii) are arranged into a plurality of rows that are each linear in shape and parallel to one another,
       a second brain wave measuring unit that comprises an electrode, is joined to the first brain wave measuring unit, and is configured to contact the first ear, and
       a first speaker unit configured to be inserted into the first ear,
    the second brain wave measuring device includes
       a third brain wave measuring unit that is configured to contact the second ear, the third brain wave measuring unit comprising a plurality of electrodes that either (i) each have a linear, elongate shape and are parallel to one another or (ii) are arranged into a plurality of rows that are each linear in shape and parallel to one another,
       a fourth brain wave measuring unit that comprises an electrode, is joined to the third brain wave measuring unit, and is configured to contact the second ear, and
       a second speaker unit configured to be inserted into the second ear, the terminal device associates with one another each of (i) the brain wave measurement result, (ii) sounds played through the first and second speaker units and (iii) a location of the user, and the terminal device generates a playlist for the user of sounds to be played through at least one of the first and second speaker units based on a location of the user input by the user and a desired brain wave state input by the user.

13. The information processing system according to claim 12, wherein in a case in which a failure occurs in one of either the first brain wave measuring device or the second brain wave measuring device, the transmitter transmits a brain wave measurement result from the other device in which a failure has not occurred to the terminal device.

14. The information processing system according to claim 12, further comprising:

a cable that connects the first brain wave measuring device and the second brain wave measuring device, wherein information is transmitted and received between the first brain wave measuring device and the second brain wave measuring device through the cable.

15. The information processing system according to claim 14, wherein the first brain wave measuring device additionally includes a battery, the first brain wave measuring device is driven by electric power supplied from the battery, and the second brain wave measuring device is driven by electric power supplied from the battery of the first brain wave measuring device to the second brain wave measuring device through the cable.

16. The information processing system according to claim 15, wherein the transmitter transmits a brain wave measurement result obtained by the second brain wave measuring device while the battery is charging.

17. The information processing system according to claim 15, wherein the first speaker unit is configured to be driven by electric power supplied from the battery, the second speaker unit is configured to be driven by electric power supplied from the battery through the cable, the first brain wave measuring device additionally includes a first support member that supports the first speaker unit, and a first ear hook unit which is joined to the first support member and which is configured to be hooked onto the first ear, the first brain wave measuring unit is provided on an outer circumference of the first speaker unit, the second brain wave measuring unit is provided on the first ear hook unit, the second brain wave measuring device additionally includes a second support member that supports the second speaker unit, and a second ear hook unit which is joined to the second support member and which is configured to be hooked onto the second ear, the third brain wave measuring unit is provided on an outer circumference of the second speaker unit, and the fourth brain wave measuring unit is provided on the second ear hook unit.

18. The information processing system according to claim 14, wherein the transmitter includes a first transmitter provided in the first brain wave measuring device, and a second transmitter provided in the second brain wave measuring device, and in a case in which a failure occurs in the cable, the first transmitter transmits a brain wave measurement result of the first brain wave measuring device to the terminal device, and the second transmitter transmits a brain wave measurement result of the second brain wave measuring device to the terminal device.

19. The information processing system according to claim 12, further comprising:

a transmission controller that controls transmission by the transmitter, wherein the transmitter includes a first transmitter provided in the first brain wave measuring device, and a second transmitter provided in the second brain wave measuring device, and in a case in which a failure occurs in one of either the first transmitter or the second transmitter, the transmission controller causes the other transmitter in which a failure has not occurred to transmit a brain wave measurement result to the terminal device.

* * * * *